United States Patent [19]

Haugland et al.

[11] Patent Number: 5,436,134
[45] Date of Patent: Jul. 25, 1995

[54] CYCLIC-SUBSTITUTED UNSYMMETRICAL CYANINE DYES

[75] Inventors: Richard P. Haugland; Stephen T. Yue; Paul J. Millard, all of Eugene; Bruce L. Roth, Corvallis, all of Oreg.

[73] Assignee: Molecular Probes, Inc., Eugene, Oreg.

[21] Appl. No.: 90,890

[22] Filed: Jul. 12, 1993

Related U.S. Application Data

[63] Continuation-in-part of Ser. No. 47,683, Apr. 13, 1993, abandoned.

[51] Int. Cl.$^6$ .......................... C12Q 1/04; C12Q 1/68; G01N 33/00; C07H 1/00
[52] U.S. Cl. .......................................... 435/34; 435/6; 435/29; 435/39; 435/4; 436/94; 436/800; 536/26.73; 536/1.11; 536/25.6
[58] Field of Search .................. 435/34, 6, 29, 32, 33, 435/4, 39; 536/27, 28, 26.73, 1.11, 25.6; 558/161; 436/94, 800

[56] References Cited

U.S. PATENT DOCUMENTS

| | | | |
|---|---|---|---|
| 2,269,234 | 1/1942 | Sprague | 260/304 |
| 4,544,546 | 10/1985 | Wang et al. | 435/6 |
| 4,883,867 | 11/1989 | Lee et al. | 536/28 |
| 4,937,198 | 6/1990 | Lee et al. | 436/94 |
| 4,997,928 | 3/1991 | Hobbs, Jr. | 435/6 |
| 5,057,413 | 10/1991 | Terstappen et al. | 435/6 |

FOREIGN PATENT DOCUMENTS

0410806A1 1/1991 European Pat. Off.
0453197A1 10/1991 European Pat. Off.
2074340 10/1981 United Kingdom.

OTHER PUBLICATIONS

Nucleic Acids Research, vol. 20, No. 11, (Rye et al.) pp. 2803–2812.
Kudinova, et al., Chemical Abstracts 93:241180j (1993).
Kudinova, et al. Khim. Geterotsikl. Soedin. 7, 903 (1980).
Simbera, et al., Chemical Abstracts 89:112299y (1978).
Brooker, et al., J Am. Chem. Soc. 64, 199 (1942).
Griffiths, Colour and Constitution of Organic Molecules, p. 241 Academic Press (1976).
Hamer, "The Cyanine Dyes and Related Compounds," The Chemistry of Heterocyclic Compounds, vol. 18, A. Weissberger, Ed., Interscience, New York (1964)* (copy not available for enclosure).
Heterocyclic Compounds, vol. 4, R. C. Elderfield ed., John Wiley and Sons Inc., (1952) pp. 1–331.
Wawzonek, et al., J. Heterocyclic Chem., 25, 381 (1988).
Marson, Tetrahedron, 48, 3659 (1992).
Rye, et al., Nucleic Acids Res., 20, 2803 (1992).
Houben-Weyl Methodon Der Organischen Chemie, Band V/ld, 231–299 (1972).

Primary Examiner—Michael G. Wityshyn
Assistant Examiner—Louise N. Leary
Attorney, Agent, or Firm—Allegra J. Helfenstein; Anton E. Skaugset

[57] ABSTRACT

The invention describes the preparation and use of fluorescent stains for nucleic acids derived from unsymmetrical cyanine dyes. In particular, the invention describes unsymmetrical cyanine dyes having a saturated or unsaturated cyclic substituent. The dyes of the invention possess superior fluorescent characteristics when complexed with nucleic acids, and have utility in any application which requires detection of nucleic acids. The presence of the cyclic substituent results in improved permeability in a wide range of living cells, resulting in improved detection of intracellular nucleic acids.

54 Claims, No Drawings

CYCLIC-SUBSTITUTED UNSYMMETRICAL CYANINE DYES

This application is a continuation-in-part of Ser. No. 08/047,683 filed Apr. 13, 1993, now abandoned.

FIELD OF THE INVENTION

The invention relates to fluorescent stains for nucleic acids derived from unsymmetrical cyanine dyes. In particular, the invention relates to relatively non-fluorescent unsymmetrical cyanine dyes having a saturated or unsaturated cyclic substituent, that form a fluorescent complex in combination with nucleic acid polymers.

BACKGROUND INFORMATION

Fluorescent dyes are known to be particularly suitable for biological applications in which a highly sensitive detection reagent is desirable. Dyes that are able to preferentially bind to a specific biological ingredient in a sample enable the researcher to determine the presence or quantity of that specific ingredient. In addition, specific biomolecules can be monitored with respect to their spatial and temporal distribution in diverse environments. It is an object of this invention to describe fluorescent dyes that form a highly fluorescent complex with desirable spectral properties when combined with nucleic acids. It is a further object of this invention to describe the use of the fluorescent characteristics of the nucleic acid-dye complex to detect, identify, and quantify nucleic acids in a variety of media. It is an additional object of this invention to describe the detection, identification and quantification of nucleic acids when they are present in a variety of cells and cell types.

In many areas of basic research there is a need for rapid and sensitive detection of nucleic acids. Typically, this involves the analysis of complex mixtures of DNA, RNA, or nucleic acid fragments. In many fields of life sciences research, including biological, biomedical, genetic, fermentation, aquaculture, agricultural, forensic and environmental research, there is a need to identify nucleic acids both within and without cells as a routine component of standard experimental methods. A common example is the widespread use of gel electrophoresis for characterizing DNA, one limitation of which is the sensitivity of the staining method used to detect the faintest bands. Biological researchers and medical researchers often need to identify intracellular nucleic acids. Many scientists and medical technicians have a need to sort cells based on the amount of nucleic acid present in the cells. The amount of nucleic acid present in the cells can be indicative of the type of cells, or even the presence of disease states in cells (e.g. nucleated human red blood cells). Such applications require a fast, sensitive and selective methodology that can detect nucleic acids, even when bounded (or surrounded) by cellular membranes.

A generally applicable dye for staining nucleic acids preferably has the following properties:

1. The nucleic acid-dye complex should exhibit a very high signal with a low background, allowing the sensitive detection of minute quantities of nucleic acids, both cell-free and intracellularly.

2. A very high signal with a low background should be attainable with a low ratio of dye to nucleic acid. The small amount of dye binding to the nucleic acid should interfere as little as possible with the essential characteristics of the nucleic acids.

3. The nucleic acid/dye complex should exhibit photostability so that the fluorescent signal may be observed, monitored and recorded without significant photobleaching.

For specific applications involving live cells, additional necessary properties for a nucleic acid stain include:

4. The dye should be permeable to cell membranes so that it can bind nucleic acids sequestered in live cells.

5. The dye should require only brief incubation with the cells to obtain a detectable signal, and be relatively non-toxic to living cells, such that staining will not disrupt the normal metabolic processes of cells or result in premature cell death.

The dyes of the present invention have utility in any current application for detection of nucleic acids that requires a sensitive detection reagent. In particular, the dyes are useful for the detection of cell-free isolated nucleic acids, nucleic acids in solution, and nucleic acid bands in gels. Additionally, the present dyes greatly increase the sensitivity of detection of nucleic acids in a variety of cells and tissues, both living and dead, plant and animal, eukaryotic and prokaryotic. This family of dyes displays unusually good photostability and appear to be relatively non-toxic to cells. Furthermore, many of the dyes rapidly penetrate cell membranes of a variety of cells. The superior properties exhibited by these dyes were neither anticipated nor obvious in view of the known unsymmetrical cyanine dyes.

Although certain unsymmetrical cyanine dyes were first described before the genetic role of nucleic acids was established (Booker, et al., *J. AM. CHEM. SOC.* 64, 199 (1942)), a variety of unsymmetrical cyanine dyes have now been found to be very effective in the fluorescent staining of DNA and RNA. U.S. Pat. Nos. 4,554,546 (to Wang, et al. 1985) and 5,057,413 (to Terstappen et al. 1991) disclose use of similar thioflavin compounds as nucleic acid stains. The nondimeric unsymmetric cyanine dye sold under the tradename Thiazole Orange has particular advantages in the quantitative analysis of immature blood cells or reticulocytes (U.S. Pat. No. 4,883,867 to Lee, et al. (1989)) or in preferentially staining the nucleic acids of bloodborne parasites with little staining of nucleated blood cells (U.S. Pat. No. 4,937,198 to Lee et al. (1990). Although Thiazole Orange and other thioflavin cyanine dyes are permeant to many mammalian cells, these dyes are impermeant to some eukaryotic cells. Other related cyanine dye compounds are described in copending applications DIMERS OF UNSYMMETRICAL CYANINE DYES (Set. No. 07/761,177 to Yue, et al. filed Sep. 16, 1991) now abandoned, UNSYMMETRICAL CYANINE DYES WITH CATIONIC SIDE CHAIN (Ser No. 07/833,006 to Yue, et al. filed Feb. 8, 1992) now U.S. Pat. No. 5,321,130, and DIMERS OF UNSYMMETRICAL CYANINE DYES CONTAINING PYRIDINIUM MOIETIES (Ser. No. 08/043,665 to Yue, et al. filed Apr. 5, 1993) now U.S. Pat. No. 5,410,030. These dyes are non-permeant to living cells, unless the cell membrane has been disrupted.

The inventors have discovered that attachment of various cyclic structures to a parent unsymmetrical cyanine produces a hmily of superior nucleic acid dyes. Like other unsymmetrical cyanine dyes, this new family of dyes exhibits extremely low fluorescence in the absence of nucleic acids, and a large fluorescence enhancement when bound to nucleic acids. The compounds of the present invention, however, show certain advantages for nucleic acid detection with respect to the known cyanine dyes. Surprisingly, although bulkier, the new dyes more quickly penetrate the cell membranes of a wider variety of cell types, including both gram-positive and gram-negative bacteria, yeasts, and eukaryotic cells as well as prokaryotic cells. The subject dyes also more rapidly stain electrophoretic gels used for the separation of nucleic acids. Direct comparison of the rate of uptake in bacteria with known dyes such as Thiazole Orange and its homologs, shows enhanced uptake of the new compounds (Table 1). Moreover, bacteria stained with the unsymmetrical dyes with cyclic substituents may exhibit greater than tenfold more fluorescence than bacteria stained with Thiazole Orange (Table 2, normalized data in Table 3). Even in applications where cell permeability is not a factor, the quantum yield of most of these dyes is unexpectedly, and significantly, better than that of Thiazole Orange (Table 4). Furthermore, by simple synthetic modification, a family of dyes having absorption and emission spectral properties that cover most of the visible and near-infrared spectrum can be prepared. The improved fluorescent properties of the dyes of the present invention, in combination with nucleic acids, present significant advantages in all areas of nucleic acid detection.

SUMMARY OF THE INVENTION AND DESCRIPTION OF PREFERRED EMBODIMENTS

The invention includes the family of unsymmetric cyanine dyes of the formula

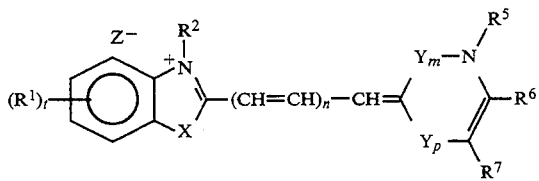

The dye can be considered in three pans: 1) A first heterocyclic ring system that is a substituted benzazolium ring system, 2) a linking roethine bridge and 3) a second heterocyclic ring system that is a pyridinium or quinolinium ring system, one or more sUbstituents of which must be an OMEGA.

An OMEGA is a saturated or unsaturated, substituted or unsubstituted, cyclic substituent that has a total of 2-16 ring carbon atoms in 1-2 alicyclic, heteroalicyclic, aromatic, or heteroaromatic rings containing 1-4 heteroatoms (wherein the hetero atoms are O, N or S) that is directly bonded to the pyridinium or quinolinium ring system by a single bond. OMEGAs that are alicyclic ring systems may be either linked or fused. Examples of OMEGA are substituted or unsubstituted cyclohexyls, cyclohexenyls, morpholinos, and piperidinyls. Examples of OMEGA that are aromatic include substituted or unsubstituted naphthyls, phenyls, thionyls, benzothiazolyls, furanyls, oxazolyls, benzoxazolyls, and pyridinyls. Substituents on OMEGA are independently hydrogen, halogen, alkyl, perfluoroalkyl, amino, alkylamino, dialkylamino, alkoxy or carboxyalkyl, each alkyl having 1-6 carbons. Preferred embodiments of OMEGA are substituted or unsubstituted naphthyl, phenyl, thienyl, morpholino, and cyclohexyl, more preferably substituted or unsubstituted phenyl.

Although $R^1$ on the benzazolium ring system is usually H, incorporation of a non-hydrogen substituent $R^1$ can be used to fine tune the absorption and emission spectrum of the resulting dye. For instance when $R^1$ is methoxy (compound 770) its absorption spectrum shifts ~12 nm and its emission spectrum shifts ~18 nm (Table 5) relative to the comparable compound where $R^1$ is H (compound 63). The benzazole may contain more than one substituent $R^1$, which may be the stone or different (t=1–4). Each $R^1$ is optionally an alkyl group having from 1-6 carbons; or a trifluoromethyl; or a halogen; or $-OR^8$, $-SR^8$ or $-(NR^8R^9)$ where $R^8$ and $R^9$, which can be the same or different, are independently H or alkyl groups having 1-6 carbons; or 1-2 alicyclic, heteroalicyclic, aromatic, or heteroaromatic rings having a total of 3-16 ring atoms (wherein the hetero atoms are O, N or S); or $R^8$ and $R^9$ taken in combination are $-(CH_2)_2-L-(CH_2)_2-$ where $L=-O-$, $-NR^{10}$, $-CH_2-$ or a single bond where $R^{10}$ is H or 1-6 carbons. Typically, the compound contains no more than one $R^1$ that is not H.

The substituent $R^2$ is an alkyl group having 1-6 carbons, preferably methyl or ethyl, more preferably methyl.

The counterion $Z^-$ is a biologically compatible ion that is stable and synthetically accessible. As used herein, a substance that is biologically compatible is not toxic as used, and does not have a substantially deleterious effect on biomolccules. Examples of $Z^-$ include, among others, chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Preferred $Z^-$ counterions are chloride, iodide, perchlorate and various sulfonates.

X is one of O, S, Se or $NR^{15}$, where $R^{15}$ is H or an alkyl group having 1-6 carbons. Alternatively, X is $CR^{16}R^{17}$, where $R^{16}$ and $R^{17}$, which may be the same or different, are independently having 1-6 carbons, or the carbons of $R^{16}$ and $R^{17}$ taken in combination complete a five or six membered saturated ring. In preferred embodiments, $R^{16}$ and $R^{17}$ are methyls.

The methine bridge consists of 1, 3 or 5 methine ($-CH=$) groups that bridge the benzazolium portion of the molecule and the pyridinium portion in such a way as to permit extensive electronic dclocalization. When n=0 the dyes are unsymmetrical monomethine dyes; when n=1 the dyes are trimethine dyes; when n=2, the dyes are pentamcthine dyes. It has been recognized from studies involving similar compounds that the number of methine groups between the heteroaromatic rings has a considerable influence on the spectral properties of the dye (Griffiths, COLOUR AND CONSTITUTION OF ORGANIC MOLECULES, pp. 241 Academic Press (1976)). We have confirmed this property for the subject dyes (Table 5).

The N-bound substituent $R^5$ is an alkyl, alkenyl, polyalkenyl, alkynyl or polyalkynyl group having 1-6 carbons; or $R^5$ is an OMEGA. Most commonly $R^5$ is an OMEGA.

The pyridinium or quinolinium ring system contains a ring fragment Y that is $-CR^3=CR^4-$, with subscripts p and m equal to 0 or 1, such that p+m=1. For all embodiments, the ring contains a 6 membered pyridinium-bascd hctcrocycle according to one of these formulations

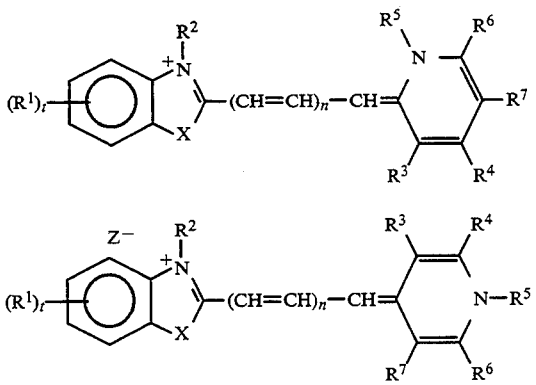

In preferred embodiments of the invention, m=1 and p=0 (4-pyridinium).

The substituents on the second heterocyclic ring system, $R^3$, $R^4$, $R^6$ and $R^7$, may be the same or different and are independently H; or an alkyl, alkenyl, polyalkenyl, alkynyl or polyalkynyl group having 1-6 carbons; or a halogen; or —OH, —$OR^8$, —$SR^8$, —($NR^8R^9$), as defined previously; or —$OSO_2R^{19}$ where $R^{19}$ is alkyl having 1-6 carbons, or perfluoroalkyl having 1-6 carbons, or aryl; or an OMEGA (defined above); or $R^6$ and $R^7$ taken in combination are —$(CH_2)_v$— where v =3 or 4, :forming a fused 5 or 6 membered ring, or $R^6$ and $R^7$, taken in combination form a fused 6 membered aromatic ring.

Where $R^6$ and $R^7$ taken in combination form a fused 6 membered aromatic ring, embodiments of this invention are quinolinium derivatives containing a fused aromatic ring according to the formula

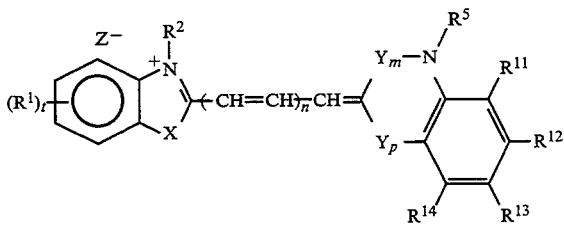

where ring substituents $R^{11}$, $R^{12}$, $R^{13}$, and $R^{14}$ may be the same or different, and are independently H; or an alkyl, alkenyl, polyalkenyl, alkynyl or polyalkynyl group having 1-6 carbons; or a halogen; or —OH, —$OR^8$, —$SR^8$, —($NR^8R^9$), where $R^8$ and $R^9$ are as defined previously; or —$OSO_2R^{19}$ where $R^{19}$ is alkyl having 1-6 carbons, or perfluoroalkyl having 1-6 carbons, or aryl; or an OMEGA. A preferred embodiment of the invention is a quinolinium wherein m=1 and p=0 (4-quinolinium).

For all embodiments of the invention, one or more of the substituents of the pyridinium or quinolinium ring system must be an OMEGA. Preferably, one or two substituents are OMEGAs. When more than one OMEGA is bound to a compound of the present invention, the two or more OMEGAs may be the same or different. For embodiments of the invention that contain pyridinium ring systems, OMEGA is preferably $R^5$, or $R^6$ or both. For embodiments of the invention that contain a 4-quinolinium ring system, OMEGA is preferably $R^4$ or $R^5$, or both. For embodiments of the invention that contain a 2-quinolinium ring system, OMEGA is preferably $R^5$, $R^{11}$ or both. For all embodiments of the invention, preferably $R^5$ is an OMEGA.

One embodiment of the invention contains exactly two non-hydrogen substituents on the second heterocyclic ring, one of which is an OMEGA. In preferred embodiments, $R^5$ is an OMEGA. In additional preferred embodiments of the invention, $R^5$ is an OMEGA and the substituent adjacent to $R^5$ ($R^6$ for pyridiniums, $R^4$ for 4-quinoliniums, and $R^{11}$ for 2-quinoliniums) is a non-hydrogen substituent. In one embodiment the substituent adjacent to $R^5$ is halogen, —$OR^8$, —$SR^8$, —$NR^8R^9$, or —$OSO_2R_{19}$, more preferably halogen. In another embodiment of the invention, $R^5$ is —$OR^8$, —$SR^8$, or —$NR^8R^9$, preferably $NR^8R^9$. In yet another embodiment of the invention, the substituent adjacent to $R^5$ is an OMEGA. $R^8$ and $R^9$ are as defined previously.

Method of Use

The use of the invention comprises combining a dye of the present invention with a sample that contains a nucleic acid, incubating the sample for a time sufficient to obtain a detectable fluorescent response, and observing the fluorescent response.

Typically, the dye is present as a staining solution, which is prepared by addition of the dye to an aqueous solution that is biologically compatible with the sample. The staining solution is made by dissolving the dye directly in an aqueous solvent such as water, a buffer solution, such as phosphate buffered saline, or an organic water-miscible solvent such as dimethylsulfoxide (DMSO), dimethylformamide (DMF), or a lower alcohol such as methanol or ethanol, or acetonitrile. Typically the dye is preliminarily dissolved ill an organic solvent (preferably DMSO) at a concentration of greater than about 100-times that used in the staining solution, then diluted one or more times with an aqueous solvent such as water or buffer. Preferably, the dye is dissolved in about 100% DMSO and then diluted one or more times in water or buffer such that the dye is present in an effective amount. An effective amount of dye is the amount sufficient to give a detectable fluorescent response when in the presence of nucleic acids. Typically staining solutions for cellular samples have a dye concentration greater than about 0.1 nM, and less than about 100 μM, more typically greater than about 1 nM. Staining solutions for electrophoretic gels typically have a dye concentration of greater than about 1 μM and less than about 10 μM, more typically about 4-5 μM. It is generally understood in the art that the specific concentration of the staining solution is determined by the physical nature of the sample, and the nature of the analysis being performed.

The dye is combined with a sample that contains a nucleic acid. The nucleic acid in the sample may be either RNA or DNA, or a mixture thereof. When the nucleic acid present is DNA, the DNA may optionally be single-, double-, triple-, or quadruple-stranded DNA. The nucleic acid may be either natural (biological in origin) or synthetic (prepared artificially). The nucleic acid may be present as nucleic acid fragments, oligonucleotides, or nucleic acid polymers. The nucleic acid may be present in a condensed phase, such as a chromosome. The presence of the nucleic acid in the sample may be due to a successful or unsuccessfifl experimental methodology, undesirable contamination, or a disease state. Nucleic acid may be present in all, or only part, of a sample, and the presence of nucleic acids may be used to distinguish between individual samples, or to differentiate a portion or region within a single sample.

The nucleic acid may be enclosed in a biological structure, for example contained within a viral particle, an organelle, or within a cell. Cell types include, but are not limited to, eukaryotes, such as nucleated plant and animal cells (Examples 43 and 46), and prokaryotes, such as bacteria, yeast, fungi, mycobacteria and mycoplasma (Examples 39, 40, 50 and 51). The nucleic acids enclosed in biological structures may be obtained from a wide variety of environments, including cultured cells, organisms or tissues, unfiltered or separated biological fluids (such as urine, cerebrospinal fluid, blood (Examples 44 and 45), lymph fluids, tissue homogenate, mucous, saliva, stool, or physiological secretions (Example 42)), or environmental samples such as soil, water and air. The nucleic acid may be endogenous or introduced as foreign material, such as by infection or by transfection. The dyes can also be used for staining nucleic acids in a cell or cells that is fixed and treated with routine histochemical or cytochemical procedures.

Alternatively, the nucleic acid is not enclosed within a biological structure, but is present as a sample solution. The sample solution can vary from one of purified nucleic acids to crude mixtures such as cell extracts, biological fluids and environmental samples. In some cases it is desirable to separate the nucleic acids from a mixture of biomolecules or fluids in the solution prior to combination with the dye. Numerous techniques exist for separation and purification of nuclcic acids from generally crude mixtures with other proteins or other biological molecules. These include such means as electrophoretic techniques and chromatographic techniques using a variety of supports.

The sample may be combined with the staining solution by any means that facilitates contact between the dye and the nucleic acid. The contact can occur through simple mixing, as in the case where the sample is a solution. The dye may be added to the nucleic acid solution directly or may contact the solution on an inert matrix such as a blot or gel, a testing strip, or any other solid or semi-solid surface, for example where only a simple and visible demonstration of the presence of nucleic acids is desired. Any inert matrix used to separate the sample can be used to detect the presence of nucleic acids by observing the fluorescent response on the inert matrix. While the subject dyes have shown an ability to permeate cellular membranes rapidly and completely upon addition of the dye solution, any other technique that is suitable for transporting the dye across cell membranes with minimal disruption of the viability of the cell and integrity of cell membranes is also a valid method of combining the sample with the subject dye. Examples of suitable processes include action of chemical agents such as detergents, enzymes or adenosine triphosphate; receptor- or transport protein-mediated uptake; pore-forming proteins; microinjection; electroporation; hypoosmotic shock; or minimal physical disruption such as scrape loading or bombardment with solid particles coated with or in the presence of the dyes.

The sample is incubated in the presence of the dye for a time sufficient to form the fluorescent nucleic acid-dye complex. Detectable fluorescence in a solution of nucleic acids is essentially instantaneous. Detectable fluorescence within cell membranes requires the permeation of the dye into the cell. In general, visibly detectable fluorescence can be obtained in a wide variety of cells with embodiments of the present invention within about 15 minutes of combination with the sample, commonly within about 5 minutes. Preferred embodiments give detectable fluorescence inside cells in less than about 2 minutes. When goat peripheral blood lymphocytes are loaded with 5 $\mu$M dye solutions, the fluorescent response is visible in less than 5 seconds,. rendering the response too fast to measure by conventional fluorometry. This property of the subject dyes is invaluable for the flow cytometric analysis of live cells, and can also be used for observing nuclear structure and rearrangement, for example such as occurs during mitosis or apoptosis. While permeation and fluorescence is rapid for all embodiments, it is readily apparent to one skilled in the art that the time necessary for sufficient permeation of the dye, or sufficient formation of the nucleic acid complex, is dependent upon the physical and chemical nature of the individuai sample and the sample medium.

The nearly universal permeability of the instant dyes, their accelerated rate of uptake and the low toxicity of the dyes to living systems enable the examination of nucleic acids in living samples with little or no perturbation caused by the dye itself (Examples 39, 40 and 50). Organisms which can be probed using the dyes of the present invention include bacteria, yeasts, fungi and mycoplasma (Examples 39, 40, 50 and 51). Conventional staining of the spores of basidiomycetes (a class of fungi that include mushrooms and puffballs) is variable in that some spores will stain while other spores do not. Those spores that can be labeled are stained most effectively by the nucleic acid stain hexidium (Copending application Ser. No. 08/063,870 filed May 17, 1993 by Haugland). In contrast, a dye of the present invention stains all basidiomycetes spores brightly (Example 47).

Similar to other unsymmetric cyanine dyes, the dyes of the present invention bind non-covalently with nucleic acids, and exhibit enhanced fluorescence upon binding, the level of enhancement being generally on the order of about 100–1000 fold, typically greater than about 300-fold (Table 4). As shown in Tables 4 and 5, the dyes of the present invention exhibit improved quantum yields upon binding to nucleic acids, relative to Thiazole Orange. These improvements in quantum yield translate directly into improved sensitivity in nearly every area of nucleic acid detection. The nucleic acid concentration in a sample can also be quantified, as the fluorescence of the nucleic acid-dye complex is linearly dependent on concentration (Example 49). While not every embodiment of the dye will show an improved quantum yield relative to a previously known nucleic acid stain, other attributes of the dyes of the present invention represent a significant improvement in an additional aspect of the method, including enhanced permeation, enhanced rate of permeation, or the selectivity of excitation and emission bands to suit specific instrumentation.

To facilitate the detection of the nucleic acid-dye complex, the excitation or emission properties of the fluorescent complex are utilized. For example, the sample is excited by a light source capable of producing light at or near the wavelength of maximum absorption of the fluorescent complex, such as an ultraviolet or visible lamp, an arc lamp, a laser, or even sunlight. Preferably the fluorescent complex is excited at a wavelength equal to or greater than about 300 nm, more preferably equal to or greater than about 340 nm. The fluorescence of the complex is detected qualitatively or quantitatively by detection of the resultant light emission at a wavelength of greater than about 400 nm, preferably greater than about 500 nm, more preferably at greater than about 480 nm. The emission is detected by means that include visible inspection, photographic film, or the use of current instrumentation such as fluorometers, quantum counters, plate readers, epifluorescence microscopes (Examples 43 and 48) and flow cytometers (Example 44), or by means -for amplifying the signal such as a photomultiplier.

When used for poststaining electrophoresis gels, the high sensitivity of the dyes of the present invention allow the detection of previously unmeasureable amounts of nucleic acids. One embodiment of the invention, when used in conjunction with an ultra-violet transilluminator, allows detection of as little as 20 picograms of double-stranded DNA per band. The commonly available equipment for excitation of samples near 254 nm, between 300 and 3 10 nm, and near 365 nm can be used to excite any of the dyes of the present invention. Excitation by a source more appropriate to the maximum absorption band of the nucleic acid-dye complex, such as an argon laser, results in even higher sensitivity. The dyes of the invention are useful for the detection of single-stranded DNA, as well as triple-stranded and quadruple-stranded DNA.

The wavelengths of the excitation and emission bands of the dyes vary with dye composition to encompass a wide range of illumination and detection bands. This allows the selection of individual dyes for use with a specific excitation source or detection filter. In particular, dyes can be selected that possess excellent correspondence of their excitation band with the 488 nm band of the commonly used argon laser (Example 44), or emission bands which are coincident with preexisting filters (Examples 39, 40, 41, 43).

The sensitivily, permeability, and instrumental utility of the dyes of the present invention provide substantial utility in the application of nucleic acid detection. The ability to detect or quantify nucleic acids in any solution, on any substrate, and from any type of sample, offers unparalleled opportunities for the use of fluorescence technology.

TABLE 1

| | Loading Time (sec) | | | |
| | To peak | | To Equilibrium | |
| Dye | S. aureus $T_{0.5}$ | E. coli $T_{0.5}$ | S. aureus $T_{0.95}$ | E. coli $T_{0.95}$ |
| --- | --- | --- | --- | --- |
| 61 | 3.4 | 18.2 | 66.9 | 270.9 |
| 63 | 7.9 | ND | 172.2 | ND |
| 613 | 9.1 | 11.3 | 149.0 | 163.1 |
| 619 | 7.3 | 15.5 | 34.3 | 243.3 |
| 624 | 7.6 | 24.3 | 27.6 | 89.4 |
| 628 | 19.6 | 36.8 | 47.2 | 89.9 |
| 591 | 6.3 | 25.3 | 116.3 | 73.3 |
| 634 | 14.5 | 12.5 | 86.3 | 154.2 |
| 73 | 10.0 | 23.3 | 145.1 | 58.6 |
| 720 | 6.8 | 21.6 | 216.4 | 221.6 |
| Thiazole Orange | 57.2 | 39.2 | 242.0 | 125.9 |

The loading time is expressed in two ways: as time required to reach half of the maximal fluorescence ($T_{0.5}$) and as the time required to reach 95% of the fluorescence measured at equilibrium ($T_{0.95}$). Temperature affects a number of different mechanisms that influence cell loading times. Preferably, the dye solution is combined with the sample at a temperature optimal for growth of bacteria in the sample within the operating parameters of the dyes, which fall between about 5 ° C. and about 50 ° C. Typically, the bacterial optimal growth temperature is about room temperature (23 ° C.).

TABLE 2

| | Fluorescence/Cell (ex 485 nm/em 530 nm)[1] | | | | | | | | |
| | Dye[2] | | | | | | | | |
| Samples[3] | 61 | 63 | 613 | 619 | 624 | 628 | 591 | 634 | Thiazole Orange |
| --- | --- | --- | --- | --- | --- | --- | --- | --- | --- |
| B. cereus | 196 | 93 | 242 | 827 | 709 | 613 | 58 | 154 | 51 |
| M. luteus | 49 | 33 | 75 | 149 | 162 | 149 | 375 | 58 | 21 |
| S. pyogenes | 0.01 | 0.01 | 0.02 | 0.06 | 0.05 | 0.04 | <0.01 | 0.03 | <0.01 |
| S. aureus | 15 | 5 | 10 | 47 | 44 | 34 | 3 | 15 | 3.2 |
| E. coli | 10 | 6 | 12 | 26 | 24 | 28 | 2 | 4 | 2 |
| S. oranienburg | 10 | 4 | 10 | 18 | 15 | 19 | 2 | 5 | 1 |
| K. pneumonia | 10 | 5 | 10 | 12 | 17 | 20 | 2 | 4 | 3 |
| S. sonnei | 6 | 3 | 6 | 13 | 11 | 16 | 1 | 4 | 1 |
| P. aeruginosa | 5 | 3 | 6 | 16 | 14 | 14 | 1 | 3 | 2 |

[1]Measured in a fluorescence microtiter plate reader with excitation and emission filters at 485 +/− 10 nm and 530 +/− 12 nm, respectively. Fluorescence data are corrected for cell number; but are not corrected for cell volume or nucleic acid content.
[2]Optimal dye concentrations as determined experimentally.
[3]Suspension concentrations from 1 × 10^5 to 3 × 10^11 cfu/mL).

TABLE 3

| | | | Normalized Fluorescence/cell (ex 485 nm/em 530 nm) | |
| Dye | QY | Normalized QY | Escherichia coli | Staphylococcus aureus |
| --- | --- | --- | --- | --- |
| Thiazole Orange | 0.18 | 1.0 | 1 | 1.0 |
| 61 | 0.46 | 2.5 | 5 | 4.7 |
| 63 | 0.24 | 1.3 | 3 | 1.6 |
| 613 | 0.33 | 1.8 | 6 | 3.1 |
| 619 | 0.62 | 3.4 | 13 | 14.7 |
| 624 | 0.58 | 3.2 | 12 | 13.8 |
| 628 | 0.40 | 2.2 | 14 | 10.6 |
| 591 | 0.09 | 0.5 | 1 | 0.9 |
| 634 | 0.18 | 1.0 | 2 | 4.7 |

TABLE 4

| | Ex/Em (nm) | | Properties on DNA | | | | |
| DYE | DNA[1] | RNA[1] | $K_p$[2] | QY[3] | P.B.[4] | F.E.[5] | RNA F.E.[5] |
| --- | --- | --- | --- | --- | --- | --- | --- |
| 61 | 500/527 | 510/530 | 1.0E07 | 0.46 | 1.10 | 353 | 502 |
| 63 | 514/531 | 515/537 | 3.9E06 | 0.24 | 1.08 | 582 | 696 |

TABLE 4-continued

| | Ex/Em (nm) | | Properties on DNA | | | | |
|---|---|---|---|---|---|---|---|
| DYE | DNA[1] | RNA[1] | $K_p$[2] | QY[3] | P.B.[4] | F.E.[5] | RNA F.E.[5] |
| 613 | 506/523 | 508/529 | 5.3E06 | 0.33 | 1.14 | 225 | 1614 |
| 619 | 488/517 | 492/529 | 9.7E06 | 0.62 | 0.89 | 301 | 518 |
| 624 | 480/501 | 485/505 | 5.0E06 | 0.58 | 1.17 | 661 | 1435 |
| 628 | 488/506 | 490/510 | 7.0E06 | 0.40 | 1.13 | 771 | 166 |
| 591 | 509/532 | 517/536 | 4.8E06 | 0.09 | 1.11 | 169 | 653 |
| 634 | 510/530 | 511/533 | 2.0E06 | 0.18 | 1.10 | 176 | 122 |
| 73 | 508/525 | 510/531 | 4.4E06 | 0.31 | 1.12 | 700 | 371 |
| 720 | 487/507 | 490/523 | 1.2E07 | 0.52 | 1.09 | 1330 | 107 |
| Thiazole Orange | 510/530 | 509/535 | 4.8E06 | 0.18 | 1.01 | 143 | 811 |

[1]Fluorescence spectra obtained using a standard ratio of 50 μM bp of DNA (bases of RNA) to 1 μM dye (standard solution) in Tris buffered saline (10 mM Tris base, 1 mM EDTA and 50 mM NaCl), pH 7.4, in a spectrophotometer (absorbance), or in a fluorometer (emission) using 10-fold less dye and nucleic acid.
[2]The dye's DNA partition coefficient ($K_o$ was determined by linear fitting of plots of reciprocal fluorescence enhancement versus reciprocal DNA concentration, as measured on a microtiter plate fluorescence reader (CytoFluor ™, Millipore).
[3]Quantum yield (QY) of dye on DNA (standard solution in Tris buffered saline, as above, adjusted to pH 10) in comparison with fluorescein, which is assumed to have a quantum yield of 0.92 under the test conditions.
[4]Photobleaching (P.B.), expressed as the residual fluorescence from the new dye relative to that of fluorescein under identical conditions. A 0.05 OD standard solution in Tris buffered saline (as above) is illuminated at 485 nm (ex. bandwidth of 20 nm) and fluorescence is measured at time 0 and 30 min. Fraction of new dye fluorescence after 30 minutes is divided by fraction of fluorescein fluorescence remaining under identical conditions.
[5]Fluorescence enhancement (F.E.) is the fluorescence of the standard solution (as above) divided by the fluorescence of the same dye in the absence of nucleic acids (both measured in plastic cuvettes).

TABLE 5

| DYE | EX max EM max | QY (DNA) | QY (RNA) | Kp |
|---|---|---|---|---|
| Thiazole Orange | 510/530 | 0.18 | 0.15 | 4.8 E6 |
| 61 | 500/527 | 0.46 | 0.34 | 1.0 E7 |
| 63 | 514/531 | 0.24 | | 3.9 E6 |
| 64 | 450/523 | | | |
| 71 | 508/526 | 0.31 | | |
| 72 | 515/535 | 0.026 | | 1.2 E6 |
| 73 | 508/525 | 0.31 | | 4.4 E6 |
| 200 | 739/759 | | | |
| 542 | 510/527 | | | |
| 578 | 470/504 | | | 4.1 E5 |
| 582 | 516/533 | | | |
| 591 | 509/532 | 0.09 | 0.13 | 4.8 E6 |
| 613 | 506/523 | 0.33 | | 5.3 E6 |
| 616 | 471/510 | | | 3.8 E5 |
| 619 | 488/517 | 0.62 | 0.22 | 9.7 E6 |
| 621 | 635/656 | | | |
| 624 | 480/501 | 0.58 | 0.57 | 5.0 E6 |
| 628 | 488/506 | 0.40 | | 7.0 E6 |
| 630 | 517/544 | 0.19 | | |
| 633 | 489/508 | 0.12 | | 7.4 E5 |
| 634 | 510/530 | 0.18 | | 2.0 E6 |
| 637 | 601/622 | 0.28 | | |
| 639 | 513/548 | 0.20 | | 8.0 E6 |
| 640 | 471/516 | | | |
| 641 | 503/526 | 0.35 | | 2.0 E7 |
| 672 | 586/611 | | | |
| 720 | 487/507 | 0.52 | | 1.2 E7 |
| 742 | 570/611 | | | |
| 752 | 494/518 | 0.51 | | |
| 758 | 504/524 | 0.44 | | 8.5 E6 |
| 760 | 483/510 | 0.68 | | |
| 764 | 486/508 | 0.58 | 0.46 | 1.1 E7 |
| 765 | 506/524 | 0.50 | | 1.1 E7 |
| 770 | 526/549 | | | 1.7 E6 |
| 774 | 517/533 | | | 7.9 E6 |
| 776 | | 0.65 | | |
| 780(Cl) | 513/536 | 0.09 | | 3.4 E6 |
| 780(S) | | 0.31 | | |
| 830 | 517/533 | | | |
| 834 | 486/507 | | | |
| 835 | 495/518 | | | |
| 853 | 516/555 | | | |
| 854 | 483/520 | | | |
| 856 | 502/523 | 0.43 | | |
| 5103 | 511/530 | 0.18 | | 5.4 E6 |
| 6104 | 505/523 | 0.52 | | 1.3 E7 |

TABLE 6

| DYE # | X | heterocycle | R[1] | R[2] | R[4] | R[5] | R[11] | R[12] | n |
|---|---|---|---|---|---|---|---|---|---|
| 125 | S | 2-pyridinium | H | Me | H | phenyl | — | — | 0 |
| 578 | S | 4-pyridinium | H | Me | Cl | phenyl | — | — | 0 |
| 616 | S | 4-pyridinium | H | Me | Cl | o-MeO-phenyl | — | — | 0 |
| 640 | S | 4-pyridinium | H | Me | H | phenyl | — | — | 0 |
| 742 | S | 4-pyridinium | H | Me | n-butyl | phenyl | — | — | 1 |
| 64 | S | 2-quinolinium | H | Me | H | phenyl | H | H | 0 |
| 61 | S | 4-quinolinium | H | Me | n-butyl | phenyl | H | H | 0 |
| 63 | S | 4-quinolinium | H | Me | H | phenyl | H | H | 0 |
| 71 | S | 4-quinolinium | H | Me | n-butyl | thienyl | H | H | 0 |
| 72 | S | 4-quinolinium | H | Me | H | Me | phenyl | H | 0 |
| 73 | S | 4-quinolinium | H | Me | H | cyclohexyl | H | H | 0 |
| 130 | S | 4-quinolinium | H | Me | —NH-phenyl | phenyl | H | H | 0 |
| 100 | S | 4-quinolinium | H | Me | n-butyl | phenyl | H | H | 2 |
| 200 | S | 4-quinolinium | H | Et | Cl | phenyl | H | H | 0 |
| 542 | S | 4-quinolinium | H | Me | H | cyclohexenyl | H | H | 0 |
| 582 | S | 4-quinolinium | H | Me | Cl | p-MeO-phenyl | H | H | 0 |
| 591 | S | 4-quinolinium | H | Me | Cl | phenyl | H | H | 0 |
| 613 | S | 4-quinolinium | H | Me | Me | phenyl | H | H | 0 |
| 619 | S | 4-quinolinium | H | Me | —NEt$_2$ | phenyl | H | H | 0 |
| 621 | S | 4-quinolinium | H | Me | n-butyl | phenyl | H | H | 1 |
| 624 | O | 4-quinolinium | H | Me | n-butyl | phenyl | H | H | 0 |

TABLE 6-continued

| DYE # | X | heterocycle | $R^1$ | $R^2$ | $R^4$ | $R^5$ | $R^{11}$ | $R^{12}$ | n |
|---|---|---|---|---|---|---|---|---|---|
| 628 | S | 4-quinolinium | H | Me | —OMe | phenyl | H | H | 0 |
| 630 | S | 4-quinolinium | H | Me | phenyl | phenyl | H | H | 0 |
| 633 | O | 4-quinolinium | H | Me | Cl | phenyl | H | H | 0 |
| 634 | S | 4-quinolinium | H | Me | H | n-hexyl | H | H | 0 |
| 637 | O | 4-quinolinium | H | Me | n-butyl | phenyl | H | H | 1 |
| 639 | S | 4-quinolinium | H | Me | phenyl | Me | H | H | 0 |
| 641 | S | 4-quinolinium | H | Me | —SMe | phenyl | H | H | 0 |
| 672 | O | 4-quinolinium | H | Me | —OMe | phenyl | H | H | 1 |
| 720 | S | 4-quinolinium | H | Me | —OEt | phenyl | H | H | 0 |
| 752 | S | 4-quinolinium | H | Me | morpholinyl | Me | H | H | 0 |
| 758 | S | 4-quinolinium | Cl | Me | n-butyl | phenyl | H | H | 0 |
| 760 | S | 4-quinolinium | H | Me | —NEt$_2$ | phenyl | H | —OMe | 0 |
| 764 | S | 4-quinolinium | H | Me | —O-iPr | phenyl | H | H | 0 |
| 765 | S | 4-quinolinium | H | Me | cyclohexyl | phenyl | H | H | 0 |
| 770 | S | 4-quinolinium | —OMe | Me | H | phenyl | H | H | 0 |
| 774 | S | 4-quinolinium | H | Me | Br | phenyl | H | H | 0 |
| 776 | S | 4-quinolinium | H | Me | —N-nPr$_2$ | phenyl | H | H | 0 |
| 780(Cl) | S | 4-quinolinium | H | Me | Cl | cyclohexyl | H | H | 0 |
| 780(S) | S | 4-quinolinium | H | Me | —SMe | cyclohexyl | H | H | 0 |
| 830 | S | 4-quinolinium | H | Me | Cl | thienyl | H | H | 0 |
| 834 | S | 4-quinolinium | H | Me | F | phenyl | H | H | 0 |
| 835 | S | 4-quinolinium | H | Me | —O-phenyl | phenyl | H | H | 0 |
| 853 | S | 4-quinolinium | H | Me | —S-2-pyridyl | phenyl | H | H | 0 |
| 854 | S | 4-quinolinium | H | Me | —OSO$_2$CF$_3$ | phenyl | H | H | 0 |
| 856 | S | 4-quinolinium | H | Me | N-Me-piperazyl | phenyl | H | H | 0 |
| 5103 | S | 4-quinolinium | H | Me | Cl | phenyl | H | —OMe | 0 |
| 6104 | S | 4-quinolinium | H | Me | cyclohexyl | Me | H | H | 0 |

Synthesis

A useful synthetic route to the dyes of the present invention can be described in three parts, following the natural breakdown in the description of the compounds. In general, the synthesis of these dyes requires three precursors: a benzazolium salt, a pyridinium (or quinolinium) salt (both of which have the appropriate chemical substituents), and (where n=1 or 2) a source for the methine spacer. Although the combination that enables these compounds to be useful stains for nucleic acids has not been described previously, the chemistry that is required to prepare and combine these precursors so as to yield any of the subject derivatives is generally well-understood by one skilled in the art. Although there are many possible variations that may yield an equivalent result, we provide herein some useful general methods for their synthesis and incorporation of chemical modifications.

The benzazolium moiety

A wide variety of derivatives of this type for use in preparing photographic dyes have been described, in particular by Brooker and his colleagues (Brooker, et al., *J. AM. CHEM. SOC.*, 64, 199 (1942)). These synthetic precursors have the common structure:

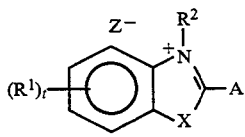

If X is O, the precursor compound is a benzoxazolium; if X is S it is a benzothiazolium; if X is Se it is a benzoselcnazolium; if X is N or an alkyl substituted N it is a benzirnidazolium; and if X is $CR^{16}R^{17}$ (where $R^{16}$ and $R^{17}$, which may be the same or different, are independently alkyl groups having 1-6 carbons, or $R^{16}$ and $R^{17}$ taken in combination complete a five or six membered saturated ring) then it is an indolinium derivative. Commonly $R^{16}$ and $R^{17}$ are both methyl. However, methods for preparing compounds where $R^{16}$ and $R^{17}$ are not methyl are known (Hamer, "The Cyanine Dyes and Related Compounds", *THE CHEMISTRY OF HETEROCYCLIC COMPOUNDS*, Vol. 18, A. Weissberger, Ed., Interscience, New York (1964) (incorporated by reference)). The commercial availability of suitable starting materials and relative ease of synthesis make compounds with X=O or S the preferred intermediates.

$R^1$ is usually incorporated in the parent benzazole molecule prior to quaternization with an alkylating agent. $R^2$ is usually obtained by alkylation of the parent heterocycle with an alkylating agent $R^2$-Z where $R^2$ is an alkyl group having 1-6 carbons and Z is an electronegative group that frequently becomes the counterion on the resultant dye. $Z^-$ is a biologically compatible counterion that additionally is stable and synthetically accessible. The counterion may be exchanged for another counterion by methods known in the art, such as the use of ion exchange resins or by precipitation. Examples of $R^2$-Z include methyl iodide, diethyl sulfate, and hexyl-p-toluenesulfonate. Preferred $R^2$-Z are compounds that yield $R^2$ =methyl, such as methyl iodide, methyl methanesulfonate, dimethyl sulfate, methyl trifluoromethanesulfonate or methyl p-toluenesulfonate.

A is a substituent whose nature is determined by the synthetic method utilized to couple the benzazolium precursor with the pyridinium or quinolinium precursor. When n=0, A is usually alkylthio, commonly methylthio, or A is chloro, bromo or iodo. When n=1 or 2, A is methyl. Only in the case of A=methyl is any part of A incorporated in the final compound.

The pyridinium or quinolinium moiety

The strongly conjugated ring system of the compounds of the present invention allows resonance stabilization of the single positive charge on the ring atoms to be distributed over the entire molecule. In particular, the charge is stabilized by partial localization on the heterocyclic nitrogen atoms of the dye. As the subject dye is drawn herein, the positive charge is formally localized on the benzazolium portion of the dye. However, it is commonly understood that a comparable resonance structure can be drawn in which the positive charge is formally localized on the pyridinium portion of the dye. Consequently we will usually refer to this portion of the molecule as a pyridine, pyridinium, quinoline or qninolinium moiety, although in the resonance structure shown it would formally be termed a dihydropyridine.

Compounds containing the qninolinium moiety in this invention differ from those that contain only the single pyridinium ring only in the presence of an additional aromatic ring containing four carbon atoms which is fused at the $R^6$ and $R^7$ positions of the parent structure. Consequently we will usually refer to this portion of the dye as the pyridine or pyridinium portion; however, except where reference is to a specific pyridine or pyridinium salt, it is understood that mention of pyridines or pyridinium salts encompasses benzopyridincs and bcnzopyridinium salts, which are formally called quinolines or quinolinium salts. Mention of quinolines and quinolinium salts refer only to structures containing two fused aromatic rings.

In the synthesis of the dyes of the invention, the second heterocyclic precursor is usually a pyridinium salt that is already appropriately substituted. Less commonly, substituents can be incorporated into the pyridinium structure subsequent to attachment of the benzazolium portion of the dye. One of the substituents, which may be incorporated before or after incorporation of the pyridinium precursor, is an OMEGA.

Aside from the structural differences between pyridines and quinolines, there exist two major structural distinctions within the family of dyes described in the invention, related to the point of attachment of the pyridinium moiety. In one case (where $m=0$ and $p=1$) the position of attachment places the methine bridge adjacent to the heterocyclic atom (2-pyridines). In the more common case (where $m=1$ and $p=0$) the position of the nitrogen atom is separated from the position of attachment of the methine bridge by what is formally a carbon-carbon double bond $Y_M$ that completes the pyridinium ring (4-pyridines). In all cases $m+p=1$; that is, if $m=1$, $p=0$ and if $m=0$, $p=1$.

Typically the required pyridinium salt precursor has the structure

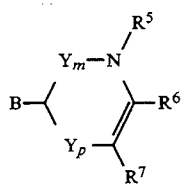

and the quinolinium salt precursor has the general structure

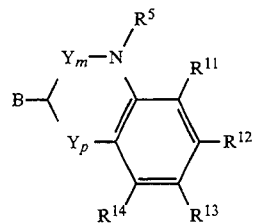

where the ring fragment Y is $-CR^3=CR^4-$, with snbscripts p and m equal to 0 or 1, such that $p+m=1$. At all times, the ring is a 6 merebored pyridinium-bascd heterocycle.

When $n=0$, B is methyl, or B is chloro, bromo or iodo. When $n=1$ or 2, B is methyl. Only when $n=1$ or $n=2$ is any part of B incorporated in the final compound.

There are several methods for the synthesis of the pyridinium portion of the dye. As the pyridinium structure contains the greatest possible variation in structure, as well as possible combinations of substituents, several routes to the pyridinium salt are possible, and in fact necessary.

The pyridinium and quinolinium precursors generally can be generated from the corresponding pyridine or quinoline by alkylation at nitrogen using a suitable alkylating agent $R^5$-Z. However, 2- and 4-pyridones and 2- and 4-quinolones are much more versatile chemical intermediates, with the added advantage of being easily prepared. For this reason, the preferred route to the pyridinium or quinolinium precursor will utilizes the corresponding pyridone or quinolone.

Useful methods for generation of the pyridone or quinolone intermediate include:

1) The condensation of an appropriately substituted aniline with diketene or its equivalent, followed by acid cyclization (*HETEROCYCLIC COMPOUNDS, VOL. 4*, R. C. Elderfield ed., John Wiley and Sons Inc., (1952) pp 1-331).

2) An Ullmann coupling between a 2- or 4-hydroxypyridone, or 2- or 4-hydroxyquinoline and an aryl halide. (Wawzonek et al., *J. HETEROCYCLIC CHEM.*, 25, 381 (1988))

The resulting pyridone or quinolone can be further modified synthetically to create the desired pyridinium or quinolinium precursor by a variety of methods, dependent upon the location of the substituent OMEGA.

When $R^5$ is an OMEGA, the pyridone or quinolone can be treated with a powerful nucleophile such as a Grignard or an alkyl lithium reagent, to generate the pyridinium or quinolinium salt after acid-catalyzed dehydroxylation. Useful examples of strong nucleophiles include, but are not limited to, metal salts of alkanes such as butyl lithium (Example 10), methyl lithium (Example 29), phenyl lithium (Example 30), or cyclohexyl magnesium chloride (Example 31). For the case in which the desired 2- or 4-substituent is hydrogen, the pyridone or quinolone can be reduced with a reducing agent such as diisobutylaluminum hydride (Examples 21 and 32) to the corresponding alcohol, which is then dehydroxylated.

The pyridone or quinolonc can also be convened to a pyridinium or quinolinium salt by using a strong halogenating agent such as phosphorous oxychloride (Example 7) phosphorous tribromide (Example 8) or diethylaminosulfur trifluoride (Example 38). The resulting activated intermediate can be condensed with the appropriate benzazolium salt to form the dye directly (Examples 7, 8, 17, 22 and 38). In the event that other substituents are desirable, the halopyridinium or haloquinolinium can be readily convened by using an appropriate reagent. For instance, treatment with alcohols or alkoxides yield alkoxy derivatives (Example 9), treatment with thiols yield thioether derivatives, and treatment with amines yield amino derivatives (Example 33). When the substituent at the 2 or 4 position is dialkylamino, the alkyl groups present on the dialkylamine can be the same or different, or when taken in combination may form a heteroalicyclic ring. For example, when the halopyridinium or haloquinolinium is treated with morpholine, the resulting substituent is a 6-membered heterocyclic ring containing nitrogen and oxygen atoms. This method can be used to attach a second OMEGA substituent as well, as when the halocompound is treated with phenol to yield the phenoxide compound, or aniline to yield an anilino derivative.

When it is desired that the product dye have an $R^5$ substituent which is not an OMEGA, the desired OMEGA substituent can be introduced via the pyridone or quinolone intermediate as well. The 2-or 4-pyridone or 2- or 4-quinolone can be generated as above from treatment of the appropriate N-substituted aniline with diketene or its equivalent followed by acid catalyzed cyclization (Example 3) or by direct alkylation of the hydroxypyridone or hydroxyquinoline with an alkylating agent $R^5$-Z. The OMEGA substituent is then introduced at the by a strongly nucleophilic reagent, such as the magnesium or lithium salt of an OMEGA, to generate the corresponding alcohol, which is then dehydroxylated to the pyridinium or quinolinium salt in situ. For instance, treatment with phenyl lithium (Example 10) yields phenyl as an OMEGA in the 2- or 4-position. If the nucleophilic reagent is cyclohexyl magnesium chloride, the cyclohexyl is an OMEGA at the 2- or 4-position (Example 13). For an OMEGA on other positions of the molecule, the appropriately substituted aniline can be convened to the pyridone or quinolone, which then undergoes flirther transformation to the pyridinium or quinolinium salt (Example 15).

The methine bridge

The roethine bridge consists of 1, 3 or 5 roethine (—CH=) groups that bridge the benzazolium portion of the molecule and the pyridinium portion in such a way as to permit extensive electronic conjugation. The number of methine groups is determined by the specific synthetic reagents used in the synthesis.

When $n=0$, the synthesis of monomethine dyes commonly uses a combination of reagents where the methine carbon atom results from either A on the benzazolium salt or B on the pyridinium salt being methyl and the other of A or B being a reactive "leaving group" that is typically methylthio or chloro, but which can be any leaving group that provides sufficient reactivity to complete the reaction. This type of reaction to make unsymmetrical monomethine dyes from two quaternary salts was originally described by Brooker et al., supra. Whether A or B is methyl depends primarily on the relative ease of synthesis of the requisite precursor salts. Because the compounds in this invention typically contain the greatest variation on the pyridinium portion of the molecule; and furthermore, because 2-methyl and 4-methyl pyridines are usually easier to prepare than their corresponding methylthio analogs, we have usually chosen to prepare the subject monomethine dyes from precursors in which A=methylthio and B=methyl. Several descriptions of this type of reaction to prepare the subject dyes are given in the Examples. The condensing reagent in the case of monomethine dyes is typically a weak base such as triethylamine or diisopropylethylamine.

To synthesize trimethine dyes ($n=1$) both A and B are methyl. In this case the additional roethine carbon is provided by a reagent such as N-methylformanilide or ethyl orthoformate (HOUBEN-WEYL, supra). Because under certain reaction conditions these same reagents can yield symmetrical cyanine dyes that incorporate two moles of a single quaternary salt, it is important to use the proper synthetic conditions, and a suitable ratio of the carbon-providing reactant to the first quaternary salt, that will promote formation of the proper intermediate. This intermediate is treated either before or after purification with the second quaternary salt to form the asymmetric cyanine dye. If desired, the counterion $Z^-$ can be exchanged at this point. Although one can usually react either of the heteroaromatic precursor salts with the carbon-providing reagent to form the required intermediate, we have usually chosen to form the intermediate from the more readily available 2-methylbenzazolium salts as described by Brooker et al. A description of a method to synthesize a trimethinc dye is given in Example 12.

Synthesis of the pentamethine dyes ($n=2$) uses the same precursors as used to prepare the trimethine dyes, and requires the same synthetic concerns about controlling the formation of an asymmetric intermediate. The three-carbon fragment that is required for the additional atoms in the bridge comes from a suitable precursor to malonaldehyde such as 1,1,3,3-tetramethoxypropane; 1,1,3-trimethoxypropene, 3-(N-methylanilino)propenal or other reagents. The condensing agent for this reaction is usually 1-anilino-3-phenylimino- 1-propene (Sprague, supra).

Subsequent modification of dyes

As described earlier, the reactivity of the 2-halogenated pyridinium or quinolinium intermediate offers a variety of synthetic methods for attachment of various substituents at the 2-position. However, the reactivity of the 2-halo derivatives is preserved even after conjugation with the benzazolium precursor, enabling conversion of the resulting dye in which $R^4$ is halogen into the appropriate alkoxy, amino and thiolate analogs, as described above for the pyridinium and quinolinium precursors. For example when 2-chloro-1-methyl-4-[2,3-dihydro-3-methyl-(benzo-1,3-thiazol-2-yl)-methylidene]-quinolinium chloride is treated with morpholine (Example 35), the corresponding 2-morpholine substituted derivative is obtained with an OMEGA being the morpholine ($R^4$=OMEGA=morpholinyl). In a similar manner, the 2-chloro substituted dye 591 can be transformed to dye 628 by simply stirring in methanol in the presence of a base such as triethylamine (Example 9), to dye 619 with diethylamine (Example 11) or to dye 853 (Example 36) with 2-thiopyridine. Dyes can also be prepared by conversion of a 2-pyridone or 2-quinolone that has already been linked to the benzazolium moiety. For instance, 4-[2,3-dihydro-3-methyl-(benzo-1,3-thiazol-2-yl) -methylidene]-1-phenyl-1,2-dihydro-2-quinolone can be treated with phosphorous oxychloride and trifluoromethanesulfonate arthydride to generate dye 591 (Example 7) and dye 854 (Example 37) respectively.

In the structural formulae below, the substituent phenyl is represented by the symbol O, as is generally used and understood in the art.

The examples below are given so as to illustrate the practice of this invention. They are not intended to limit or define the entire scope of this invention.

Example 1: Preparation of 1,2-dihydro-4-methyl-1-phenyl-2-quinolone (1)

The following compound is prepared:

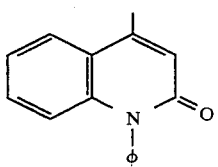

The starting 1,2-dihydro-4-methyl- 1 -phenyl-2-quinolone (1) is prepared either by an Ullmann coupling according to a literature procedure (Wawzonek et al., supra.) or via the reaction of the corresponding diarylamine with dikctene followed by acid cyclization ( Elderfield, supra). Thus 10.0 g (62.9 mmoles) of 2-hydroxy-4-methylquinoline is heated at reflux with 24.0 g (377 mmolcs) of copper powder, 8.68 g (62.9 mmoles) of potassium carbonate and 19.2 g (94 mmoles) of iodobenzene for 48 hours. The reaction is cooled to room temperature, partitioned between water and ethyl acetate, filtered, and the organic layer is dried over magnesium sulfate. The crude product is purified on a silica gel column, eluting with 1:1 ethyl acetate/hexanes to yield 8.1 g of the desired product.

Example 2: Preparation of 1.,2-dihydro-4-methyl-1-phenyl-2-pyridone (2)

The following compound is prepared:

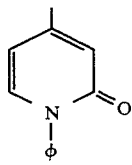

The starting 1,2-dihydro-4-methyl-1-phenyl-2-pyridone (2) is prepared as in Example 1 with a 40% yield, except that the starting material is 4-methyl-2-pyridone.

Example 3: Preparation of 1,2-dihydro-1,4-dimethyl-2-quinolone (3)

The following compound is prepared:

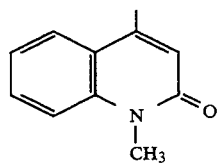

The starting 1,2-dihydro-1,4-dimethyl-2-quinolone (3) is prepared by first conjugating N-methylaniline with diketene, followed by an acid cyclization of the amide intermediate. Thus 10.0 g (0.12 moles) of diketene is added dropwise to 10.7 g (0.1 moles) of N-methylaniline and the reaction is heated at 100 ° C. for an additional 30 minutes. To the resulting mixture is added 30 mL of acetic acid and 30 mL of sulfuric acid, and the mixture is heated at 50 ° C. overnight. The reaction is worked up with water and ethyl acetate and purified on a silica gel column to yield 9.5 g of the desired product.

Example 4: Preparation of 1,2-dihydro-7-methoxy-4-methyl, 1-phenyl-2-quinolone The following compound is prepared:

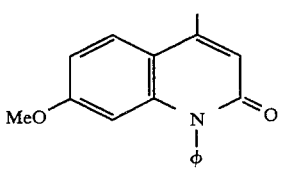

N-(3-hydroxyphenyl)-N-phcnylamine is O-methylatcd with potassium carbonate and methyl iodide in acetone in 39% yield. The resulting N-(3-methoxyphenyl)-N-phenylamine is then reacted with diketene to generate the corresponding acetoacetamide which, without purification, is cyclized in acetic acid/sulfuric acid as in Example 3 to generate the desired quinolone in 41% yield.

Example 5: Preparation of the 1,2-dihydro-1,4-dimethyl-8-phenyl-2-quinolone

The following compound is prepared:

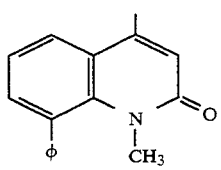

The starting material is 2-phcnylaniline, which is methylated with potassium carbonate and methyl iodide to obtain N-methyl-2-phenylaniline. The N-methyl-2-phenylaniline is treated with diketene and acid and is cyclized in acetic acid/sulfuric acid as in Example 3 to generate the desired quinolone.

Example 6: Preparation of 3-ethyl-2-ethylthiobenzothiazolium iodide

The following compound is prepared:

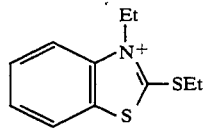

To 2.0 g of Nail (57% dispersion in oil, washed twice with hexanes) in 10 mL of DMF, 6.0 g of 2-mercaptobenzothiazole in 20 mL of DMF is added dropwise, and the mixture stirred for 10 minutes. To the sodium salt thus generated is added 6.7 g of ethyl iodide and the mixture is stirred at room temperature for one hour. The reaction is worked up with ethyl acetate and water to yield 6.6 g of the product. To 2:15 g of the 2-ethylthiobcnzothiazole thus obtained is added 3.5 g of ethyl

Example 7: Preparation of 2-chloro-4-[2,3-dihydro-3-methyl-(benzo-1,3-thiazol-2-yl)-methylidene]-1-phenylquinolinium iodide (dye 591)

The following compound is prepared:

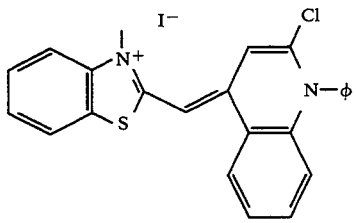

To 2.8 g (11.9 mmoles) of 1,2-dihydro-4-methyl-1-phenyl-2-quinolone (Example 1) in 20 mL of methylene chloride is added, 1.85 g of phosphorus oxychloride and a catalytic amount of dimethylformamide (Marson, TETRAHEDRON., 48, 3659 (1992)). The resulting mixture is heated to reflux for 24 hours. The reaction mixture is cooled to room temperature and 3.5 g (9.6 mmoles) of N-methyl-2-methylthiobenzothiazolium tosylate (Rye, et al., NUCLEIC ACIDS RES., 20, 2803 (1992)) is added followed by 1.3 mL (9.4 mmoles) of triethylamine. The mixture is stirred for an additional 6 hours. The crude product is purified on silica gel using ethyl acetate:chloroform:methanol, 3:3:1 as eluant. The product is then recrystallized from methanol/chloroform/ethyl acetate.

An additional synthetic rotite to this product utilizes 4-[2,3-dihydro-3-methyl-(benzo-1,3-thiazol-2-yl) -methylidene[-1,2-dihydro-1-phenyl-2-quinolone (4), which in turn is prepared from 1,2-dihydro-4-methyl-1-phenyl-2-quinolone (1) and 3-methyl-2-methylthiobenzothiazolium tosylate. Thus the lithium enolate of the (1) (prepared from treating the quinolone with 2.7 equivalent of lithium diisopropyl amide) or the silyl enolate (from (1) and trimethylsilyl trifluoromethanesulfonate and diisopropylethylamine) is stirred with the benzothiazolium tosylate. The desired intermediate (4) is isolated by column chromatography. The quinolone (4) is then treated with phosphorous oxychloride to generate the 2-chloro derivative.

Example 8: Preparation of 2-bromo-4-[2,3-dihydro-3-methyl-(benzo-1,3-thiazol-2-yl)-methylidene ]-1-phenylquinolinium iodide (dye 774)

The following compound is prepared:

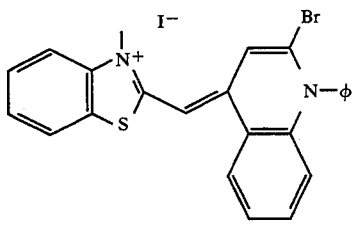

To 0.47 g (2 mmoles) of 1,2-dihydro-4-methyl-1-phenyl-2-quinolone (Example 1) in 8 mL of toluene is added, 0.6 g (2.2 mmoles) of phosphorous tribromide and the solution is heated to reflux for 30 minutes. The mixture is cooled to room temperature, diluted with 20 mL of ethyl acetate and filtered. The solid thus obtained is suspended in 15 mL of methylene chloride and added to a solution of 3-methyl-2-methylthiobenzothiazolium tosylate (0.55 g, 1.5 mmoles) and triethylamine (0.35 mL, 1.8 mmoles) in 8 mL of DMF. The reaction mixture is stirred for 30 minutes and the red solid is separated by filtration. The volatile components of the filtrate are removed under reduced pressure and the residue is purified using a silica gel column, glueing with 3:3:1 ethyl acetate/chloroform/methanol. The restrange band that has a slightly higher $R_f$ than the 2-chloro-4-[2,3-dihydro-3-methyl-(benzo-1,3-thiazol-2-yl)-methylidene]-1-quinolinium iodide (Example 7) is isolated, redissolved in about 1.5 mL of methanol and added to 1.5 g of NaI in 20 mL of water. The product is isolated by filtration as the iodide salt and dried in vacuo.

Example 9: Preparation of 2-methoxy-4-[2,3-dihydro-3-methyl-(benzo-1,3-thiazol-2-yl) -methylidene]-1-phenylquinolinium iodide (dye 628)

The following compound is prepared:

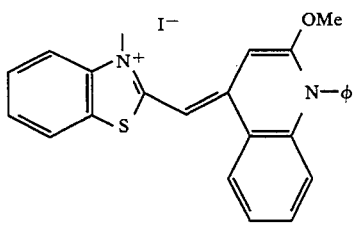

To 1.0 g (4.3 mmoles) of 1,2-dihydro-4-methyl-1-phenyl-2-quinolene (Example 1) in about 10 mL methylene chloride, 2 mL of phosphorous oxychloride is added followed by a catalytic amount of dimethylformamide. After 3 hours under reflux, all the volatile components are removed under reduced pressure. Ten mL of methanol is added to the residue, and the solution is heated for an additional 2 hours. The methanol is removed under reduced pressure, and 10 mL of methylene chloride is added, followed by 1.56 g (4.3 mmoles) of N-methyl-2-methylthiobenzothiazolium tosylate and 1.5 mL of triethylamine. The resulting mixture is stirred at room temperature for 3 days. The crude material is purified on a silica gel column by eluting with 5:5:1 ethyl acetate: chloroform: methanol.

The same dye is prepared by stirring dye 691 in methanol at room temperature in the presence of 10 equivalents of triethylamine for about one hour.

Example 10: Preparation of 2-butyl-4-[2,3-dihydro-3-methyl-(benzo-1,3-thiazol-2-yl) -methylidene]-1-phenylquinolinium iodide (dye 61)

The following compound is prepared:

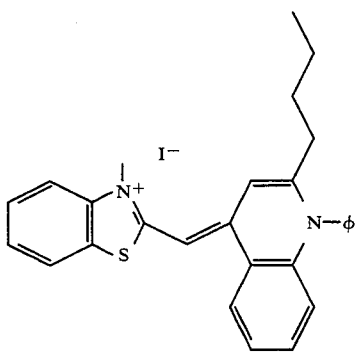

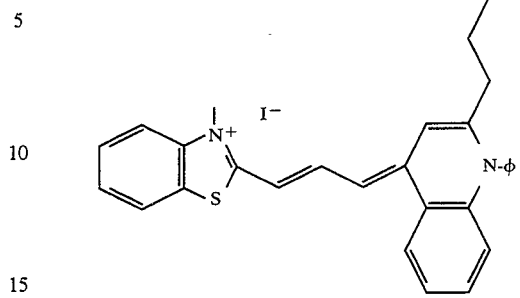

To 0.235 g (1 mmole) of 1,2-dihydro-4-methyl-1-phenyl-2-quinolone (Example 1) in 10 mL of THF at −78° C. under nitrogen, 1.2 equivalents of n-butyl lithium is introduced. The reaction is stirred at −78° C. for 15 minutes, and then the temperature is raised to 0° C. for another 30 minutes, at which time the reaction is quenched with acetic acid and all volatile components are removed under reduced pressure. The resulting residue is dissolved in 5 mL of methylene chloride and 0.367 (1 mmole) of the 4-methyl-2-methylthiobenzothiazolium tosylate is added followed by 0.28 mL (2 mmoles) of triethylamine. The reaction mixture is stirred for an additional 20 minutes at room temperature and the crude product is isolated as the iodide salt after a salt exchange. The crude iodide is recrystallized from methanol.

Example 11: Preparation of
2-diethylamino-4-[2,3-dihydro-3-methyl-(benzo-1,3-thiazol-2-yl) -methylidene]-1-phenylquinolinium iodide
(dye 619)

The following compound is prepared:

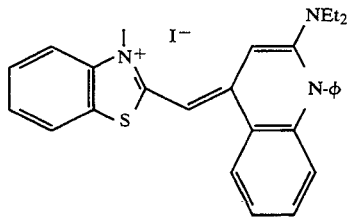

26 mg of 2-chloro-4-[2,3-dihydro-3-methyl-(benzo-1,3-thiazol-2-yl)-methylidene]-1-phenylquinolinium iodide (Example 1) is heated at 55° C. with 0.5 mL of diethylamine in 1.5 mL of DMF overnight. The desired product is isolated by a simple filtration.

Example 12: Preparation of
2-butyl-4-[(2,3-dihydro-3-methyl-(benzo-1,3-thiazol-2-yl) -propenylidene]-1-phenylquinolinium iodide (dye 621)

The following compound is prepared:

The procedure is the same as in Example 6, except that the 2-(2-anilinovinyl)-3-methylbenzothiazolium tosylate is used instead of the corresponding 3-methyl-2-methylthiobenzothiazolium tosylate. Thus to the 2-butyl-3-methyl-1-phenylquinolinium (1 mmole) generated in 10 mL of methylene chloride at room temperature is added 0.44 g (1 mmole) of 2-(2-anilinovinyl)-3-methylbenzothiazolium tosylate followed by 0.14 mL of triethylamine and 0.1 g of acetic anhydride. The reaction mixture is stirred at room temperature overnight and the crude product is isolated as the iodide salt and purified by recrystallization.

Example 13: preparation of
2-cyclohexyl-1-methyl-4-[(2,3 -dihydro-3-methyl-(benzo-1,3-thiazole-2-yl)-methylidene]-quinolinium iodide (dye 6104)

The following compound is prepared:

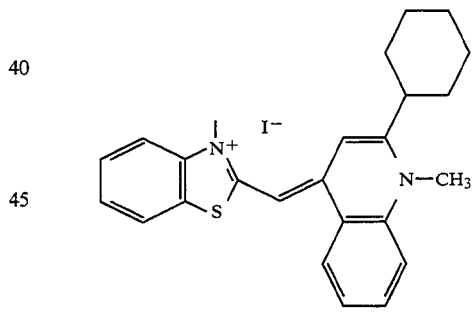

To 0.35 g (2 mmoles) of 1,2-dihydro-1,4-dimethyl-2-quinolone (Example 3) in 8 mL of THF at 0° C. is added 1.2 mL of cyclohexyl magnesium chloride (2M in ether) and stirred at the low temperature for 1 hour. At the end of the period, 0.3 mL of acetic acid is introduced and the solvent is evaporated and the residue is dried in vacuo to remove the excess acetic acid. The intermediate is redissolved in 20 mL of methylene chloride and 0.74 g (2 mmoles) of 3-methyl-2-methylthio-benzothiazolium tosylate is added followed by 0.42 mL (2.5 mmoles) of triethylamine. The reaction mixture is stirred at room temperature for 30 minutes and the chide product is purified on a silica gel column. The isolated product is dissolved in methanol and then added to 1.5 g of sodium iodide in 50 mL of water. The precipitate is recovered by filtration and is recrystallized from methanol to yield the pure product.

Example 14: Preparation of 2-chloro-7-methoxy-4-[(2,3-dihydro-3-methyl-(benzo-1,3-thiazole -2-yl)-methylidene]-1-phenylquinolinium chloride (dye 5 103)

The following compound is prepared:

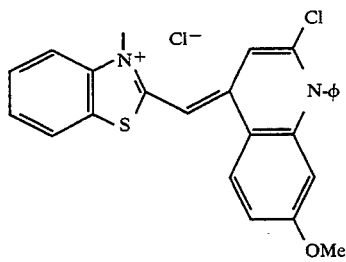

1,2-dihydro-7-methoxy-4-methyl-1-phenyl-2-quinolone (Example 4) (0.53 g, 2 mmoles) is dissolved in 10 mL of methylene chloride with 0.37 g (2.4 mmoles) of phosphorous chloride and 0.05 mL of DMF, and heated to reflux overnight. The mixture is cooled to room temperature and 0.73 g of 3-methyl-2-methylthio-benzothiazolium tosylate is introduced followed by 0.28 mL (2 mmoles) of triethylamine. The mixture is stirred for 30 minutes and the crude product is purified on a silica gel column eluting with 4:4:1 ethyl acetate/chloroform/methanol to obtain the desired product as the chloride salt.

Example 15: Preparation of 1-methyl-8-phenyl-4-[(2,3-dihydro-3-methyl-(benzo-1,3-thiazol -2-yl)-methylidene]-quinolinium iodide (dye 72)

The following compound is prepared:

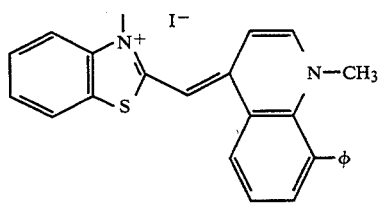

To 0.1 g (0.4 mmoles) of the quinolone (Example 5) in 5 mL of THF at 0° C., 0.5 mL of 1.0 M DIBAL (diisobutyl aluminum hydride) in cyclohexane is added and stirred 1.5 hours. At the end of the period, 1 mL of methanol is added and the volatile components are removed under reduced pressure. To the residue is added 10 mL of methylene chloride. To this organic layer, 0.16 g (0.4 mmoles) of 3-methyl-2-methylthio-benzothiazolium tosylate and 0.14 mL (1 mmole) of triethylamine are added and the resulting mixture is stirred at room temperature for 3 hours. The resulting mixture is loaded on a silica gel column and eluted with 3:3:1 ethyl acetate/chloroforum/methanol. The isolated fraction is dissolved in 2 mL of methanol and added to 1 g of NaI in 20 mL of water. The iodide salt thus obtained is further recrystallized from methanol to obtain the pure product.

Example 16: Preparation of 2-butyl-4-[5-chloro-2,3-dihydro-3-methyl-(benzo-1,3-thiazole) -2-methylidene]-1-phenylquinolinium iodide (dye 758)

The following compound is prepared:

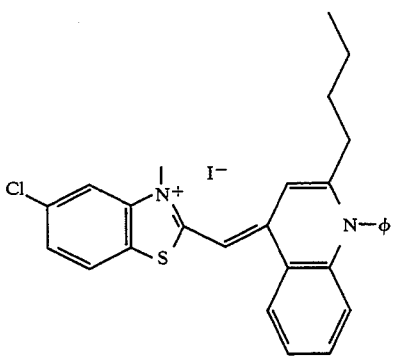

One mmole of 2-butyl-4-methyl-N-phenyl-quinolinium salt (prepared according to Example 10) and 1 mmole of 5-chloro-3-methyl-2-methylthio-benzothiazolium iodide (prepared according to a method similar to the preparation of 2-methylthio-3-methylobenzoxazolium tosylate of Example 20, starting with the commercially available 5-chloro-2-mercaptobenzothiazole) are mixed in 20 mL of methylene chloride and 1 mmole of triethylamine is introduced. The reaction mixture is worked up as in Example 20 and recrystallized from methanol/chloroform to obtain the product.

Example 17: Preparation of 4-[2,3-dihydro-3-methyl-6-methoxy-(benzo-1,3-thiazol-2-yl) -methylidene]-1-phenylquinolinium iodide (dye 670)

The following compound is prepared:

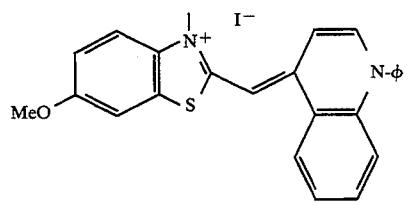

The target dye is prepared from 2,3-dimethyl-6-methoxybenzothiazolium tosylate and 4-chloro-1-phenylquinolinium chloride. Thus, 1 g (5.6 mmoles) of 6-methoxy-2-methylbenzothiazole is heated with 1.09 g (5.87 mmoles) of methyl tosylate at 90° C. to yield 1.9 g (91%) of the 2,3-dimethyl-6-methoxybenzothiazolium tosylate. The 4-chloro-1-phenylquinolinium chloride is prepared from the 1,4-dihydro-1-phenyl-4-quinolone which in turn is obtained from an Ullmann coupling reaction as above from 4-hydroxyquinoline, iodobenzene, copper powder and potassium carbonate. The quinoline (17 mg) is converted to the 4-chloro-1-phenyl-quinolinium chloride by heating with 18 mg of phosphorous oxychloride and a catalytic amount of DMF in 2 mL of toluene. The chloride is then reacted with 28 mg of 2,3-dimethyl-6-methoxybenzothiazolium tosylate (from 6-methoxy-2-methylbenzothiazole and methyl tosylate) in the presence of 0.011 mL of triethylamine to generate the product that is convened to the iodide salt and is then recrystallized from methanol to obtain the pure product.

Example 18: Preparation of 2-butyl-4-[(2,3-dihydro-3-methyl-(benzo-1,3-thiazol-2-yl) -pentadienylidene]-1-phenylquinolinium iodide (dye 100)

The following compound is prepared:

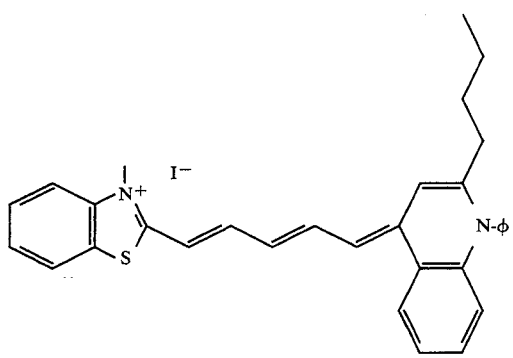

The intermediate 2-(4-anilino)-1,3-butadienyl)-benzothiazolium iodide is prepared using methods known in the art (U.S. Pat. No. 2,269,234 to Sprague (1942); and HOUBEN-WEYL METHODON DER ORGANISCHEN CHEMIE, Band V/1d, 231–299 (1972)) from 1,3-dimethylbenzothiazolium iodide and 1-anilino-3-phenylimino-1-propene hydrochloride and is coupled with the 2-butyl-3-methyl-1-phenylquinolinium to generate the corresponding near infrared absorbing dye (dye 100).

Example 19: Preparation of 2-chloro-4-[2,3-dihydro-3-ethyl-(benzo-1,3-thiazol-2-yl) -methylidene]-1-phenylquinolinium iodide (dye 200)

The following compound is prepared:

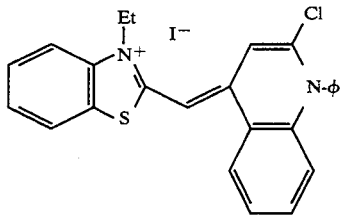

The compound is prepared as in Example 7, except that 3-ethyl-2-ethylthiobenzothiazolium iodide (Example 6) is used instead of the corresponding N-methyl-2-methylthiobenzothiazolium tosylate.

Example 20: Preparation of 2-butyl-4-[2,3-dihydro-3-methyl-(benzo-1,3-oxazol-2-yl) -methylidene]-1-phenylquinolinium iodide (dye 624)

The following compound is prepared:

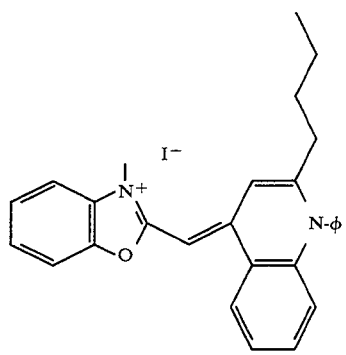

The procedure is the same as in Example 3, except that N-methyl-2-methylthiobenzoxazolium tosylate is used instead of the corresponding benzothiazolium tosylate.

Example 21: Preparation of 4-[(2,3-dihydro-3-methyl-(benzo-1,3-thiazol-2-yl)-methylidene]-1-phenylpyridinium iodide (dye 640)

The following compound is prepared:

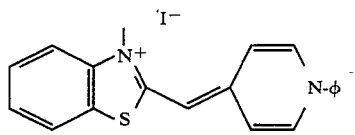

To 0.37 g (2 mmoles) of 1-phenyl-1,2-dihydro-2-pyridone in 10 mL of methylene chloride at 0° C., 2.2 mL of 1.0 M DIBAL (in cyclohexane) is added and the resulting mixture is stirred at a low temperature for 2 hours. At the end of the period, 0.3 mL of acetic acid is added, and the volatile components are evaporated under reduced pressure. The residue is dried in vacuo at about 50° C. for 1 hour. The residue is redissolved in 15 mL of methylene chloride and 0.74 g (2 mmoles) of 3-methyl-2-methylthiobenzothiazolium tosylate is added followed by 0.28 mL (2 mmoles) of triethylamine. The reaction mixture is stirred at room temperature for 3 hours and the crude product is directly loaded on a silica gel column and eluted with 3:3:1 ethyl acetate/chloroform/methanol. The fraction containing the desired product is pooled and after the evaporation of the solvent, redissolved in 5 mL of DMF and added to 5 g of sodium iodide in 75 mL of water. The precipitate is filtered and recrystallized from methanol to obtain the pure product.

Example 22: Preparation of 2-chloro-4-[(2,3-dihydro-3-methyl-(benzo-1,3-thiazol-2-yl) -methylidene]-1-phenylpyridinium chloride (dye 578)

The following compound is prepared:

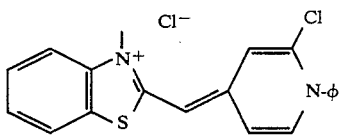

A mixture of 0.37 g (2 mmoles) of 1,2-dihydro-4-methyl-1-phenyl-2-pyridone (Example 2), 0.34 g (2.2 mmoles) of phosphorous oxychloride and 0.05 mL of DMF in 5 mL of methylene chloride are heated at 60° C. in a sealed tube overnight. The reaction mixture is cooled to room temperature and another 5 mL of methylene chloride is added followed by 2 mmoles of 3-methyl-2-methylthiobenzothiazolium tosylate and 2 mmoles of triethylamine. The reaction mixture is stirred at room temperature for 3 hours. The product is isolated by filtration as the chloride salt.

Example 23: Preparation of 2-butyl-4-[(2,3-dihydro-3-methyl-(benzo-1,3-thiazol-2-yl)-propenylidene]-1-phenylpyridinium iodide (dye 742)

The following compound is prepared:

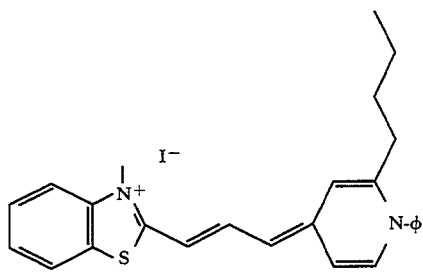

To 0.37 g (2 mmoles) of 1,2-dihydro-1-phenyl-4-methyl-2-pyridone (Example 2) in 10 mL of THF at 0° C., 1 mL of a 2.5 M n-butyl lithium in hexane is added, and solution is stirred at 0 ° C. for one hour. At the end of this period, 0.3 mL of acetic acid is added and all of the volatile components are removed under reduced pressure. The residue is dried m vacuo for several hours. To the residue is added 20 mL of methylene chloride, followed by 0.88 g (2 mmoles) of 2-(2-anilinovinyl)-3-methylbenzothiazolium tosylate, 0.35 mL (2.5 mmoles) of triethylamine and 0.2 g (2 mmoles) of acetic anhydride. The reaction mixture is stirred for one hour. The product is isolated as the iodide salt and purified using a silica gel column (3:3:1 ethyl acetate/chloroform/methanol).

Example 24: Preparation of 4-[(2,3-dihydro-3-methyl-(benzo-1,3-thiazol-2-yl)-methylidene]-1-cyclohexylquinolinium iodide (dye 73 )

The following compound is prepared:

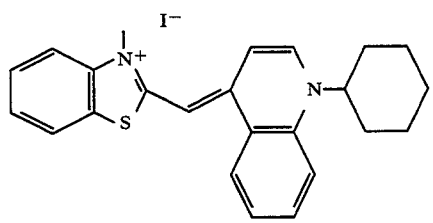

A mixture of 1.43 g (10 mmoles) of lepidine and 2.1 g (10 mmoles) of cyclohexyl iodide are heated at 130° C. for 2 hours. At the end of the period, 20 mL of ethyl acetate is added and filtered and 1.36 g of solid is obtained. The intermediate N-cyclohexyl lepidinium iodide is stirred in 50 mL of methylene chloride with 1.41 g of 3-methyl-2-methylthiobenzothiazolium tosylate and 1.12 mL of triethylamine for several hours. The crude product is converted to the iodide salt and recrystallized from methanol to yield the pure product.

Example 25: Preparation of 2-[(2,3-dihydro-3-methyl-(benzo-1,3-thiazol-2-yl)-methylidene]-1-phenylquinolinium iodide (dye 64)

The following compound is prepared:

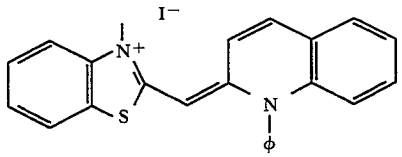

The intermediate N-phenyl-2-chloroquinolinium chloride is prepared according to the literature method (Marson, TETRAHEDRON, 48, 3659 (1992)). Thus 1.06 g (5 mmoles) of N, N-diphenyl acetamide is heated with 1.69 g (11 mmoles) of phosphorous oxychloride and 0.44 g (6 mmoles) of DMF at 120° C. for 2 hours. The reaction mixture is cooled to room temperature and 15 mL of methylene chloride is added to dissolve the residue. To the solution is added 1.68 g (5 mmoles) of N,2-dimethylbenzothiazolium tosylate and 1.46 g (12 mmoles) of 4-dimethylaminopyridine, and the reaction is stirred overnight (Elderfield, supra). The crude product is first purified on a silica gel column eluting with 2:2:1 ethyl acetate/chloroform/methanol and then metathesized to the iodide salt and recrystallized from methanol to obtain the pure product.

Example 26: Preparation of 2-chloro-4-[2,3-dihydro-3-methyl-(benzo-1,3-thiazol-2-yl) -propenylidene]-1-phenylquinolinium iodide (dye 823)

The following compound is prepared:

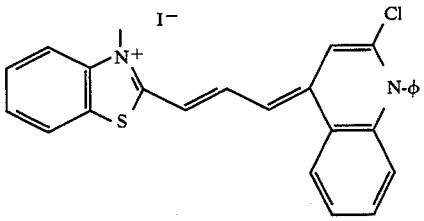

The 2-chloro-1-phenylquinolinium chloride (2 mmol) is generated in a similar manner as in Example 7 in a separate flask and dissolved in 10 mL of methylene chloride. A solution is prepared of 3-methyl-2-(2-anilinovinyl) -benzothiazolium tosylate (2 mmol) in 50 mL of methylene chloride, 0.56 mL (4 mmol) of triethylamine and 0.2 g (2 mmol) of acetic anhydride. This solution is stirred at room temperature for 30 minutes. The 2-chloro-1-phenylquinolinium chloride solution is then added and the combined solution is stirred at room temperature for 30 minutes. The organic layer is then washed with 50 mL of a 1:1 mixture of 1 N HCl/brine, and then with brine, and finally dried over magnesium sulfate. The product is isolated by column chromatography.

Example 27: Preparation of 2-chloro-4-[2,3-dihydro-3-methyl-(benzo-1,3-thiazol-2-yl)-methylidene]-1-cyclohexylquinolinium iodide (dye 780)

The following compound is prepared:

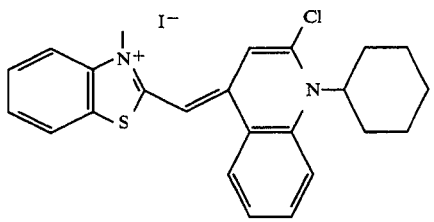

1-Cyclohexyl-1,2-dihydro-4-methyl-2-quinolone is prepared in a similar manner as in Example 4, except the starting material is N-cyclohexylaniline. The quinolone (0.482 g, 2 mmol) is transformed to the 2-chloro-1-cyclohexylquinolinium chloride with a procedure similar to Example 7, except that it is reacted with 3-methyl-2-methylthiobenzothiazolium tosylate (0.74 g, 2 mmol) and triethylamine (0.28 mL, 2 mmol) to yield the product.

Example 28: Preparation of 1,2-dihydro-4-methyl-1-(thiophen-3-yl)-2-quinolone A mixture of 0.8 g of 2-hydroxy-4-methylquinoline, 1.22 g of 3-bromothiophene, 0.69 g of potassium carbonate and 1.9 g of iodobenzene in 10 mL of DMF is heated to reflux for 16 hours. The reaction is worked up with water and ethyl acetate and the desired product is isolated by column chromatography.

Example 29: preparation of 2-methyl-4-[2,3-dihydro-4-methyl-(benzo-1,3-thiazol-2-yl)-methylidine]-1-phenylquinolinium iodide (dye 613)

The procedure is analogous to that described in Example 10 except that methyl lithium is used instead of butyl lithium.

Example 30: Preparation of 1,2-diphenyl-4-[2,3-dihydro-4-methyl-(benzo-1,3-thiazol-2-yl)-methylidene]-quinolinium iodide (dye 630)

The procedure is analogous to that described in Example 10 except that phenyl lithium is used instead of butyl lithium. Example 31: Preparation of 2-cyclohexyl-4-[2,3-dihydro-4-methyl-(benzo-1,3-thiazol-2-yl)-methylidene]-1-phenylquinolinium iodide (dye 765)

The procedure is analogous to that described in Example 10 except that cyclohexyl magnesium chloride is used instead of butyl lithium.

Example 32: Preparation of 4-[2,3-dihydro-4-methyl-(benzo-1,3-thiazol-2-yl)-methylidene]-1-phenylquinolinium (dye 63)

To 0.235 g of 1,2-dihydro-4-methyl-1-phenyl-2-quinoline (Example 1) in 10 mL of THF at −78° C., mL of a 2.5 M DIBAL in cyclohexene is introduced via syringe and the mixture is stirred at low temperature for 30 minutes, and then at 0° C. for an additional 30 minutes. At the end of that period, 0.25 mL of acetic acid is added and all the volatile components are removed under reduced pressure. The residue is dissolved in 5 mL of methylene chloride and treated with 0.37 g of 3-methyl-2-methylthiobenzothiazolium tosylate in the presence of 1 mmole of triethylamine to yield the desired product.

Example 33: Preparation of 2-diethylamino-4-[2,3-dihydro-4-methyl-(benzo-1,3-thiazol-2-yl)-methylidene]-1-phenylquinolinium iodide (dye 619)

The 2-chloro-4-methyl-1-phenylquinolinium chloride (10 mmol) is generated as described in Example 7. After all volatile components are removed under reduced pressure, the residue is dissolved in about 20 mL of methylene chloride and added dropwise to 6 mL of diethylamine in 20 mL of methylene chloride at 0° C. The mixture is stirred for 30 minutes, after which one equivalent of 3-methyl-2-methylthiobenzothiazolium tosylate (in 20 mL of DMF) is added. After stirring an additional 20 minutes the reaction is worked up with chloroform and water to yield the desired product.

Example 34: Preparation of 4-[2,3-dihydro-4-methyl-(benzo-1,3-thiazol-2-yl)-methylidene]-1-methyl-2-phenylquinolinium iodide (dye 639)

The procedure is analogous to that described in Example 32, with the exception of the use of 1,2-dihydro-1,4-dimethyl-2-quinolone (Example 3) instead of 1,2-dihydro-4-methyl-1-phenyl-2-quinolone.

Example 35: Preparation of 4-[2,3-dihydro-4-methyl-(benzo-1,3-thiazol-2-yl)-methylidene]-1-methyl-2-morpholinoquinolinium iodide (dye 752)

The quinolone (3) (0.35g, 2 mmol) (Example 3) is treated with phosphorous oxychloride and DMF as described in example 7 to generate 1-methyl-2-chloroquinolinium chloride, which is then reacted with 3-methyl-2-methylthiobenzothiazolium tosylate (2 mmol) and triethylamine (2 mmol) to yield the desired intermediate. The crude intermediate is metathesized to the iodide salt as above, and recrystallized from methanol/chloroform to generate the 2-chloro derivative. The 2-chloro derivative is then treated with an excess of morpholine in DMF at 50° C. to generate the desired product.

Example 36: Preparation of 4-[2,3-dihydro-4-methyl-(benzo-1,3-thiazol-2-yl)-methylidene]-1-phenyl-2-(2-pyridylthio)-quinolinium iodide (dye 853)

2-Mercaptopyridine (6.3 mg) is added to 25 mg of dye 591 in 2 mL of methylene chloride, followed by 13 μL of triethylamine, and the resulting mixture is stirred at room temperature for 1.5 hours. The volume of solvent is reduced to about 0.5 mL under reduced pressure and the product is isolated by filtration.

Example 37: Preparation of 4-[2,3-dihydro-4-methyl-(benzo-1,3-thiazol-2-yl)-methylidene]-1-phenyl-2-trifluoromethanesulfonyloxy-quinolinium iodide (dye 854)

Trifluoromethanesulfonic acid anhydride (66 μL) is introduced to 0.1 g of 1,2-dihydro-4-[2,3-dihydro -3-methyl-(benzo-1,3-thiazol-2-yl)-methylidene]-1-phenyl-2-quinolone (example 7) in 5 mL of 1,2-dichloroethane, and the solution is heated at 80° C. for 3 hours. The reaction is worked up with water and chloroform, and the resulting product is purified by column chromatography on silica gel.

Example 38: Preparation 2-fluoro-4-[2,3-dihydro-4-methyl-(benzo-1,3-thiazol-2-yl)-methylidene]-1-phenylquinolinium iodide (dye 834)

Diethylaminosulfur trifluoride (0.26 mL) is added to 0.47 g of 1,2-dihydro-4-methyl-1-phenyl-2-quinolone (example 1) in 5 mL of methylene chloride, and the mixture is heated at 80° C. in a sealed tube for 16 hours. The resulting solution is added to a mixture of 0.74 g of 3-methyl-2-methylthiobenzothiazolium tosylate and 0.28 mL of triethylamine in a mixed solution of 10 mL DMF and 20 mL methylene chloride. After 10 minutes of additional stirring, the reaction is washed with 1 N HCl, with NaCl and subsequently dried over magnesium chloride. The product is isolated by column chromatography on silica gel.

Example 39: Staining of live *Saccharomyces cerevisiae*, *Candida albicans* or *Neurospora crassa*

Fungal cells and yeast cells are washed by centrifugation and resuspended in a solution of 2–20% glucose, 10 mM Na-HEPES, pH 7.4 to a cell density of between $5 \times 10^5$ and $2 \times 10^6$ cells/mL. Enough of the 10 mM dye 591 stock solution in DMSO is added to effect a final concentration of 10 μM dye. The suspension is incubated for 30 min at 37° C. 15 μL are placed between coverglass and microscope slide. Cell fluorescence is observed using fluorescein (long-pass emission) or rhodamine filter sets. Dye 591 staining of live fungal and yeast cells gives rise to orange-red fluorescent variablyosized intravacuolar cylindrical bodies and little cytoplasmic background.

Example 40: Staining of live *Saccharomyces cerevisiae*

Saccharomyces cells are washed by centrifugation and resuspended in a solution of 2% glucose, 10 mM Na-HEPES, at pH 7.4 to a cell density of between $5 \times 10^5$ and $2 \times 10^6$ cells/mL. Enough of the 10 mM dye 624 or 835 stock solution in DMSO is added to effect a final concentration of 10 μM dye. The suspension is incubated for 10–30 rain at 37° C. 15 μL are placed between coverglass and microscope slide. Cell fluorescence is observed using a fluorescein filter set. Both dye 624 and dye 835 stain the mitochondria of live yeast bright green with little diffuse cytoplasmic background.

Example 41: Staining of protozoans

Five μL of a 10 mM DMSO stock solution of dye 61 is added to 5 mL of unbuffered protozoan culture. The culture plus dye is incubated for 10 min at room temperature and 15 μl of the preparation is mounted between a coverglass and slide. The preparation is observed by epifluorescence microscopy using a 100× objective lens and fluorescein long-pass filter set. The dye stains the nucleus and, to a lesser extent, the cytoplasm of several common species of ciliates. flagellates and amoebae. Bacteria in the suspension are also stained using this procedure.

Example 42: Staining of spermalozoans

A diluted suspension of goat sperm obtained in a frozen state is thawed and held at 32° C. Enough of a 10 mM dye stock solution (dye 628, 624, 835 or 591) is added to the sperm suspension to obtain a final concentration of 0.5 μM dye. The sperm are labeled by incubation in the.dye solution for 10 min. Sperm cells stain with all of the dyes, and the order of brightness is 628>624>>835>591. Motility is retained at 0.5 μM, but is lost in some of the sperm at 5 μM dye.

Example 43: Staining of nuclei of adherent cultured mammalian cells

3T3 mouse fibroblast cells are grown on coverslips in calf serum-supplemented Dulbccco's Modified Eagle medium. Coverslips of cells are washed using 135 mM NaCl, 5 mM KCl, 1 mM $MgCl_2$, 1.8 mM $CaCl_2$, 20 mM Na-HEPES, at pH 7.4 (HBSS+). Coverslips are incubated for 30 min at room temperature in solutions of dye 835 with final concentrations of either 2 μM or 0.2 μM prepared in HBSS+. Cells are then washed in HBSS+ and viewed by epifiuoresccnce microscopy using a long-pass fluorescein filter set. After 30 minutes all of the cells are stained green in both the nucleus and cytoplasm, although to different intensities, when viewed through the long-pass fluorescein filter. Cells loaded with 0.2 μM dye show distinct mitochondrial staining whereas cytoplasmic fluorescence appear to be less punctate in cells incubated with 2 μM dye. The signal to background is, however, higher in the 0.2 μM loaded cells. Nuclear staining is fairly uniform and is not concentrated in the nucleolar regions. When the dye is removed from the extracellular buffer, cell staining gradually decreases. Cell viability, as determined using an ethidium homodimcr counterstain, is maintained throughout.

Example 44: Reticulocyte analysis by flow cylometry

Blood is collected aseptically in a $K_3$EDTA-containing tube and maintained at room temperature. 5 μL of whole blood is added to 1 mL off 30–90 nM solution of dye 628 or 591 in 135 mM NaCl, 5 mM KCl, and 20 mM Na-HEPES, at pH 7.4 (HBSS−). The suspension is incubated at room temperature :for between 10 rain and 3 hr. The cells are analyzed in a flow cytometcr by gating around the erythrocyte population. Fluorescence is excited using the 488 nm line of the argon laser and emission is measured between 520 and 550 nm. Cells with fluorescence above the autofluorescence of the erythrocyte population without dye are counted as reticulocytes. Rcticulocyte staining of patient blood samples is compared with staining of reticulocyte standards (Retic Chex. Streck). Dyes 591 and 628 are effective stains for rcticulocytes, both by the measurement of commercial rcticulocyte standards and with populations of reticulocytes in normal blood and in blood from patients with hcmolytic anemia.

Example 45: Detection of *Mycobacterium* in whole blood

Whole goat blood smears are prepared with 30 μL blood diluted 50:50 with HBSS−. Blood with or without 5 μL of *Mycobacterium phlei* in 1% TX-100 per 100 μL of blood is used for the smears. Smears are air dried and heat fixed at 50° C. for 2 hours. 15 μL of 5 μM dye 628 in E-pure water are added to the smears. A coverslip is placed over the dye droplet and sealed. Bacteria are visible after <30 sec. Numerous extremely bright bacteria can be seen in blood to which Mycobacteria have been added. Low background fluorescence is observed in blood without Mycobacteria, aside from a few tiny bright dots, which are much smaller than bacteria and not nearly as bright when observed by epifluorescence microscopy using a 40× or 100× objective lens.

Example 46: Staining of plant tissue (Aucuba spp. leaf epidermal tissue)

A leaf of Aucuba spp. is cross-sectioned with a razor blade and immersed in 0.5 mL of a 10 μM solution of dye 624 in E-pure water in a 35 mm glass dish. The tissue is stained for 30 min at room temperature in the dark. The tissue preparation is mounted in the presence of dye between coverglass and slide. The leaf epidermal layer is demarcated by a large amount of yellow autofluorescence, however both the vascular bundle and cell nuclei stain bright green in the dye 624-loaded cells.

Example 47: Staining of mushroom spores

Spores are rinsed from the gills on the underside of the cap of an agaric using a stream of distilled water. The spores are concentrated by centrifugation for 30 sec at 10,000 rpm in a microfuge. A minimal volume of a 50 μM solution of dye 624 in distilled water is added. The suspension is incubated for 30 min at room temperature. A 15 μL aliquot is mounted in the presence of the dye. Dye 624 stains all spores brightly.

Example 48: Staining of Infectious Hepatic Necrosis Virus (IHNV)

Enough of a 10 mM stock solution of dye 613 is added to a suspension of IHNV in HBSS+ to result in a 40 μM working solution. The viruses are incubated in the presence of the dye for 10 minutes at 15° C. and subsequently observed in an epifluorescence microscope using a 100× objective lens. The virus particles have dimensions of approximately 30×160 nm and so are below the optical resolution limit of the microscope using visible light. Incorporation of dye 613 into the viral RNA results in a sufficient concentration of the dye in the particle to render it visible as a bright point of green light when observed using a standard fluorescein long-pass filter set.

Example 49: Measurement of DNA and RNA concentration in solution

Three dyes are used to quantify the amount of DNA or RNA in solution. Dyes 61, 619, and 624 are prepared as 10 mM stock solutions in DMSO. Stock dye solutions are diluted to 2 μM in TNE buffer consisting of 2 M NaCl, 10 mM Tris, 1 mM EDTA, adjusted to pH 7.4. Calf thymus DNA or yeast ribosomal RNA solutions between 1–40 μg/mL were prepared in TNE buffer and mixed 1:1 with diluted dye solutions. Fluorescence of 100 μL samples is measured in a CytoFluor fluorescence microplate reader (Millipore Corp.). A linear increase in fluorescence was obtained with increasing DNA or RNA concentration. Of the dyes tested, the signal is greatest with dye 61.

Example 50: Detection of Bacterial Growth

The density of a suspension of *Escherichia coli* is indicated by adding enough cells to cuvettes containing 30 μM dye 624 to effect final densities of $10^5$–$10^8$ bacterial and incubating for 5 minutes. The suspensions are excited at 480 nm and the fluorescence emission spectra of the suspensions are measured in a fluorometer (Photon Technologies International). The green fluorescence of the bacterial suspension increases with decade changes in bacterial cell density.

Example 51: Staining of Mycoplasma

A suspension of *Mycoplasma arginini* is stained for 10 minutes by adding an equal volume of a 0.2 μm membrane-filtered 20 μM dye 624 solution in HBSS—. When observed with an epifluorescence microscope with a 100× objective lens, numerous bright points are observed in the suspension after the first minute of staining and fluorescence continues to rise for at least 10 minutes after dye addition.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula

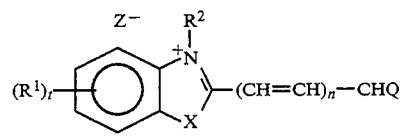

wherein:

each $R^1$ is independently H; or an alkyl group having from 1-6 carbons; or a trifluoromethyl; or a halogen; or —$OR^8$,— $SR^8$ or —($NR^8R^9$) where $R^8$ and $R^9$, which can be the same or different, are independently H; or alkyl groups having 1-6 carbons; or 1-2 alicyclic, heteroalicyclic, aromatic or heteroaromatic rings, containing 1-4 heteroatoms, wherein the hetero atoms are O, N or S; or $R^8$ and $R^9$ taken in combination are —$(CH_2)_2$—L—$(CH_2)_2$— where L=a single bond, —O—, —$CH_2$—, or —$NR^{10}$—,where $R^{10}$ is H or an alkyl group having 1-6 carbons; and t=1-4;

$R^2$ is an alkyl group having 1-6 carbons;

X is O, S, Se or —$NR^{15}$, where $R^{15}$ is H or an alkyl group having 1-6 carbons; or X is $CR^{16}R^{17}$ where $R^{16}$ and $R^{17}$, which may be the same or different, are independently alkyl groups having 1-6 carbons, or $R^{16}$ and $R^{17}$ taken in combination complete a five or six membered saturated ring;

n=0, 1 or 2;

$Z^-$ is a biologically compatible counterion;

Q has the formula Q1 or Q2

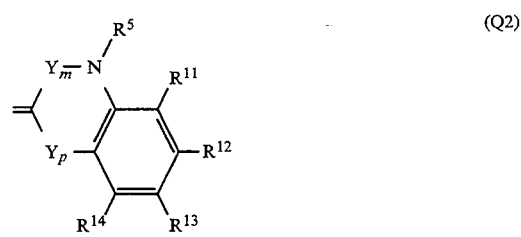

wherein

Y is —CR$^3$=CR$^4$—;

p and m=0 or 1, such that p+m=t;

R$^5$ is an alkyl, alkenyl, polyalkenyl, alkynyl or polyalkynyl group having 1-6 carbons; or R$^5$ is aa OMEGA;

R$^3$, R$^4$, R$^6$ and R$^7$, which may be the same or different, are independently H; or an alkyl, alkenyl, polyalkenyl, alkynyl or polyatlcynyl group having 1-6 carbons; or a halogen; or —OH, —OR$^8$, —SR$^8$, —(NR$^8$R$^9$); or —OSO$_2$R$^{19}$ where R$^{19}$ is alkyl having 1-6 carbons, or perfluoroalkyl having 1-6 carbons, or aryl; or an OMEGA;

or R$^6$ and R$^7$, taken in combination are —(CH$_2$)$_v$— where v=3 or 4, or R$^6$ and R$^7$ form a fused aromatic ring according to formula Q2;

R$^{11}$, R$^{12}$, R$^{13}$, and R$^{14}$, which may be the same or different, are independently H, or an alkyl, alkenyl, polyalkenyl, alkynyl or polyalkynyl group having 1-6 carbons; or a halogen; or an OMEGA; or —OH, —OR$^8$, —SR$^8$, or —(NR$^8$R$^9$);

OMEGA is a cyclohexyl, cyclohexenyl, morpholino, piperidinyl, naphthyl, phenyl, thienyl, benzothiazolyl, furanyl, oxazolyl, benzoxazolyl or pyridinyl that is unsubstituted or optionally substituted one or more times, independently, by halogen, alkyl, perfluoroalkyl, areinc, alkylamino, dialkylamino, alkoxy or carboxyalkyl, having 1-6 carbons, and that is attached as R$^3$, R$^4$, R$^5$, R$^6$, R$^7$, R$^{11}$, R$^{12}$, R$^{13}$, or R$^{14}$ by a single bond;

such that at least one of R$^3$, R$^4$, R$^5$, R$^6$, R$^7$, R$^{11}$, R$^{12}$, R$^{13}$, and R$^{14}$, is an OMEGA, and, where more than one of R$^3$, R$^4$, R$^5$, R$^6$, R$^7$, R$^{11}$, R$^{12}$, R$^{13}$, and R$^{14}$ is an OMEGA, each OMEGA is optionally the same or different; and such that when O has the formula Q1, n=O.

2. A compound according to claim 1 wherein X is O or S.

3. A compound according to claim 1 wherein each R$^1$ is H, and R$^2$ is ethyl or methyl.

4. A compound according to claim 1 wherein R$^5$ is an OMEGA.

5. A compound according to claim 1 wherein m=1.

6. A compound according to claim 1 wherein R$^5$ is an OMEGA, and R$^6$ is H; or R$^6$ is an alkyl, alkenyl, polyalkenyl, alkynyl or polyalkynyl group having 1-6 carbons; or a halogen; or R$^6$ is —OH, —OR$^8$, —SR$^8$, (NR$^8$R$^9$); or R$^6$ is —OSO$_2$R$^{19}$; or R$^6$ is an OMEGA.

7. A compound according to claim 1, wherein each R$^1$ is H, R$^3$ and R$^4$ are H, R$^2$ is ethyl or methyl, R$^5$ is an OMEGA, and R$^6$ is optionally H; or R$^6$ is an alkyl group having 1-6 carbons; or R$^6$ is a halogen; or R$^6$ iS —OH, —OR$^8$, —SR$^8$, —(NR$^8$R$^9$); or R$^6$ is —OSO$_2$R$^{19}$; or R$^6$ is an OMEGA.

8. A compound according to claim 7, wherein X=O or S.

9. A compound according to claim 7, wherein n=O or 1.

10. A compound according to claim 7, wherein m=1.

11. A compound according to claim 7, wherein R$^5$ is a substituted or unsubstituted cyclohexyl, cyclohexenyl, morpholino, piperidinyl, naphthyl, phenyl, thienyl, benzothiazolyl, furanyl, oxazolyl, benzoxazolyl or pyridinyl.

12. A compound according to claim 7, wherein R$^5$ is naphthyl or phenyl.

13. A compound according to claim 7, wherein R$^5$ is phenyl.

14. A compound according to claim 1 of the formula

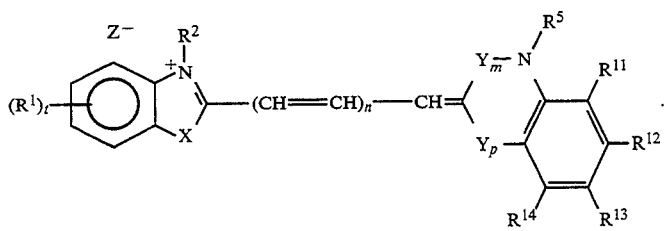

15. A compound according to claim 14, wherein R$^5$ is an OMEGA.

16. A compound according to claim 14, wherein each R$^1$ is H, R$^2$ is ethyl or methyl, X=O or S, and n=O or 1.

17. A compound according to claim 14, wherein m=1, of the structure

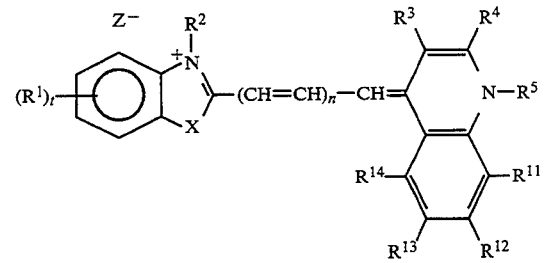

wherein each R$^1$ is independently H; or an alkyl group having from 1-6 carbons; or a trifluoromethyl; or a halogen; or —OR$^8$, —SR$^8$ or —(NR$^8$R$^9$) where R$^8$ and R$^9$, which can be the same or different, are independently H; or alkyl groups having 1-6 carbons; and t=1-4;

R$^3$, R$^4$, R$^5$, R$^{11}$, R$^{12}$, R$^{13}$, and R$^{14}$ are independently H, halogen, an alkyl containing 1-6 carbons, —OH, —OR$^8$, —SR$^8$, —(NR$^8$R$^9$), where R$^8$ and R$^9$, which may be the same or different, are independently H; or alkyl groups having 1-6 carbons; or 1-2 substituted or unsubstituted alicyclic, heteroalicyclic, aromatic, or heteroaromatic rings, containing 14 heteroatoms, wherein the heteroatoms are O, N, or S; or R$^8$ and R$^9$ taken in combination are —(CH$_2$)$_2$—L—(CH$_2$)$_2$' where L=O—, —NR$_{10}$—, —CH$_2$— or a single bond where R$^{10}$ is H or an alkyl group having 1-6 carbons; or —O-SO$_2$R$^{19}$ where R$^{19}$ is alkyl having 1-6 carbons or perfluoroalkyl having 1-6 carbons or aryl; or an OMEGA;

X is O or S; and at least one of R$^4$ and R$^5$ is an OMEGA.

18. A compound according to claim 17, wherein each R$^1$ is H, and R$^2$ is ethyl or methyl.

19. A compound according to claim 17, wherein $R^5$ is an OMEGA.

20. A compound according to claim 17 wherein $R^4$ is halogen or $-OSO_2R^{19}$.

21. A compound according to claim 17 wherein $R^4$ is $-OR^8$, $-SR^8$, or $-(NR^8R^9)$.

22. A compound according to claim 17 wherein $R^4$ is alkyl having 1-6 carbons, or is an OMEGA which is a cycloalkyl having 3-16 carbons.

23. A compound according to claim 17 wherein $R^5$ is a substituted or unsubstituted cyclohexyl, cyclohexenyl, morpholino, piperidinyl, naphthyl, phenyl, thienyl, benzothiazolyl, furanyl, oxazolyl, benzoxazolyl or pyridinyl.

24. A compound according to claim 17 wherein $R^5$ is naphthyl or phenyl.

25. A compound according to claim 17 wherein $R^5$ is phenyl.

26. A compound according to claim 17 wherein $R^3$, $R^{11}$, $R^{12}$, $R^{13}$ and $R^{14}$ are H.

27. A fluorescent complex comprising a nucleic acid and one or more dye molecules of the formula

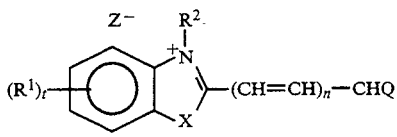

wherein:
each $R^1$ is independently H; or an alkyl group having from 1-6 carbons; or a trifluoromethyl; or a halogen; or $-OR^8$, $-SR^8$ or $-(NR^8R^9)$ where $R^8$ and $R^9$, which can be the same or different, are independently H; or alkyl groups having 1-6 carbons: or 1-2 aft cyclic, heteroalicyclic, aromatic or heteroaromatic rings, containing 1-4 heteroatoms, wherein the hetero atoms are O, N or S; or $R^8$ and $R^9$ taken in combination are $-(CH_2)_2-L-(CH_2)_2-$ where L=a single bond, $-O-$, $-CH_2-$, or $-NR_{10}-$ where $R^{10}$ is H or an alkyl group having 1-6 carbons; and t=1-4;

$R^2$ is an alkyl group having 1-6 carbons;

X is O, S, Se or $NR^{15}$, where $R^{15}$ is H or an alkyl group having 1-6 carbons; or X is $CR^{16}R^{17}$ where $R^{16}$ and $R^{17}$, which may be the same or different, are independently alkyl groups having 1-6 carbons, or $R^{16}$ and $R^{17}$ taken in combination complete a five or six membered saturated ring;

n=0, 1 or 2;

$Z^-$ is a biologically compatible counter ion;

Q has the formula Q1 or Q2

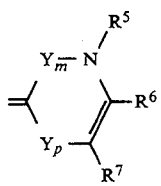

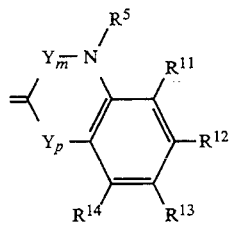

wherein
Y is $-CR^3=CR^4-$;
p and m=0 or 1, such that p+m=1;
$R^5$ is an alkyl, alkenyl, polyalkenyl, alkynyl or polyalkynyl group having 1-6 carbons; or $R^5$ is an OMEGA;
$R^3$, $R^4$, $R^6$ and $R^7$, which may be the same or different, are independently H; or an alkyl, alkenyl, polyalkenyl, alkynyl or polyalkynyl group having 1-6 carbons; or a halogen; or $-OH$, $-OR^8$, $-SR^8$, $-(NR^8R^9)$; or $-OSO_2R^{19}$ where $R^{19}$ is alkyl having 1-6 carbons, or perfluoroalkyl having 1-6 carbons, or aryl; or an OMEGA;
or $R^6$ and $R^7$, taken in combination are $-(CH_2)_v-$ where v=3 or 4, or $R^6$ and $R^7$ form a fused aromatic ring according to formula Q2;
$R^{11}$, $R^{12}$, $R^{13}$, and $R^{14}$, which may be the same or different, are independently H; or an alkyl, alkenyl, polyalkenyl, alkynyl or polyalkynyl group having 1-6 carbons; or a halogen; or an OMEGA; or $-OH$, $-OR^8$, $-SR^8$, or $-(NR^8R^9)$;
OMEGA is a saturated or unsaturated, substituted or unsubstituted, cyclic substituent that has a total of 2-16 ring carbon atoms in 1-2 alicyclic, heteroalicyclic, aromatic, or heteroaromatic rings, containing 1-4 heteroatoms wherein the hetero atoms are O, N or S, that is unsubstituted or optionally substituted one or more times, independently, by halogen, alkyl, perfluoroalkyl, alkoxy or carboxyalkyl, having 1-6 carbons, and that is attached as $R^3$, $R^4$, $R^5$, $R^6$, $R^7$, $R^{11}$, $R^{12}$, $R^{13}$, or $R^{14}$ by a single bond; such that at least one of $R^3$, $R^4$, $R^5$, $R^6$, $R^7$, $R^{11}$, $R^{12}$, $R^{13}$, and $R^{14}$ is an OMEGA, and, where more than one of $R^3$, $R^4$, $R^5$, $R^6$, $R^7$, $R^{11}$, $R^{12}$, $R^{13}$, and $R^{14}$ is an OMEGA, each OMEGA is optionally the same or different.

28. A complex according to claim 27, wherein the nucleic acid is DNA.

29. A complex according to claim 27, wherein the nucleic acid is DNA.

30. A complex according to claim 27, wherein the nucleic acid is synthetic.

31. A complex according to claim 27, wherein the nucleic acid is biological.

32. A complex according to claim 27, wherein no more than 2 of $R^3$, $R^4$, $R^5$, $R^6$, $R^7$, $R^{11}$, $R^{12}$, $R^{13}$, and $R^{14}$ is an OMEGA, and each OMEGA is optionally the same or different.

33. A complex according to claim 27, wherein OMEGA is a substituted or unsubstituted cyclohexyl, cyclohexenyl, morpholino, piperidinyl, naphthyl, phenyl, thienyl, benzothiazolyl, furanyl, oxazolyl, benzoxazolyl or pyridinyl.

34. A complex according to claim 27, wherein X is O or S.

35. A complex according to claim 27 wherein each $R^1$ is H, and $R^2$ is ethyl or methyl.

36. A complex according to claim 27 wherein $R^5$ is an OMEGA.

37. A complex according to claim 27, wherein each $R^1$ is H;
$R^3$ and $R^4$ are H, $R^2$ is ethyl or methyl;
$R^6$ is optionally H; or an alkyl group having 1-6 carbons; or a halogen; or —OH, —OR$^8$, —SR$^8$, —(NR$^8$R$^9$); or or an OMEGA;
X=O or S;
n=0 or 1;
m=1; and
$R^5$ is an OMEGA which is a substituted or unsubstituted cyclohexyl, cyclohexenyl, morpholino, piperidinyl, naphthyl, phenyl, thienyl, benzothiazolyl, furanyl, oxazolyl, benzoxazolyl or pyridinyl.

38. A complex according to claim 37, wherein $R^5$ is phenyl.

39. A complex according to claim 27 of the formula

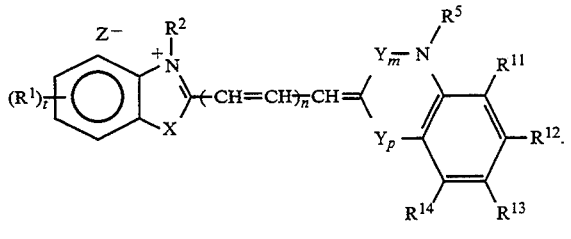

40. A complex according to claim 39, wherein each $R^1$ is H, $R^2$ is ethyl or methyl, X=O or S, n=0 or 1 and $R^5$ is an OMEGA.

41. A complex according to claim 39, wherein m=1, of the structure

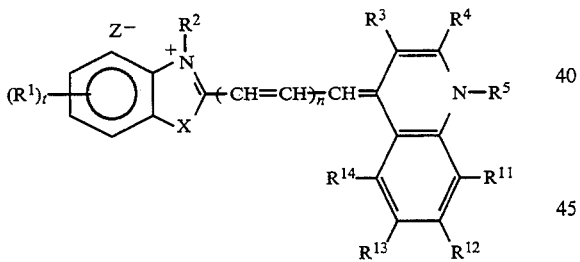

wherein each $R^1$ is independently H; or an alkyl group having from 1-6 carbons; or a trifluoromethyl; or a halogen; or —OR$^8$, —SR$^8$ or —(NR$^8$R$^9$) where $R^8$ and $R^9$, which can be the same or different, are independently H; or alkyl having 1-6 carbons; and t=1-4;
$R^3$, $R^4$, $R^5$, $R^{11}$, $R^{12}$, $R^{13}$, and $R^{14}$ are independently H, halogen, an alkyl containing 1-6 carbons, —OH, —OR$^8$, —SR$^8$, —(NR$^8$R$^9$), where $R^8$ and $R^9$, which may be the same or different, are independently H; or alkyl group having 1-6 carbons; or 1-2 substituted or unsubstituted alicyclic, heteroalicyclic, aromatic, or heteroaromatic rings, containing 1-4 heteroatoms, wherein the heteroatoms are O, N, or S; or $R^8$ and $R^9$ taken in combination are —(CH$_2$)$_2$—L—(CH$_2$)$_2$— where L=—O—, —NR$_{10}$—, —CH$_2$— or a single bond where $R^{10}$ is H or an alkyl group having 1-6 carbons; or —OSO$_2$R$^{19}$ where $R^{19}$ is alkyl having 1-6 carbons or perfluoroalkyl having 1-6 carbons or aryl;
X is O or S; and
at least one of $R^4$ and $R^5$ is an OMEGA.

42. A complex according to claim 41, wherein each $R^1$ is H, and $R^2$ is ethyl or methyl.

43. A complex according to claim 41 wherein $R^4$ is halogen or —OSO$_2$R$^{19}$.

44. A complex according to claim 41 wherein $R^4$ is —OR$^8$, —SR$^8$, or —(NR$^8$R$^9$).

45. A complex according to claim 41 wherein $R^4$ is alkyl having 1-6 carbons, or is an OMEGA which is a cycloalkyl having 3-16 carbons.

46. A complex according to claim 41 wherein OMEGA is a substituted or unsubstituted cyclohexyl, cyclohexenyl, morpholino, piperidinyl, naphthyl, phenyl, thienyl, benzothiazolyl, furanyl, oxazolyl, benzoxazolyl or pyridinyl.

47. A complex according to claim 46 wherein $R^5$ is phenyl.

48. A complex according to claim 41 wherein $R^3$, $R^{11}$, $R^{12}$, $R^{13}$ and $R^{14}$ are H.

49. A method of staining nucleic acids in a sample, comprising
a) combining a sample that contains nucleic acids with a dye compound of the formula:

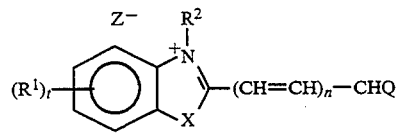

wherein:
each $R^1$ is independently H; or an alkyl group having from 1-6 carbons; or a trifluoromethyl; or a halogen; or —OR$^8$, —SR$^8$ or —(NR$^8$R$^9$) where $R^8$ and $R^9$, which can be the same or different, are independently H; alkyl groups having 1-6 carbons; or 1-2 alicyclic, heteroalicyclic, aromatic or heteroaromatic rings, containing 1-4 heteroatoms, wherein the hetero atoms are O, N or S; or $R^8$ and $R^9$ taken in combination are —(CH$_2$)$_2$—L—(CH$_2$)$_2$— where L=—O—, —NR$_{10}$', —CH$_2$— or a single bond where $R^{10}$ is H or an alkyl group having 1-6 carbons; and t=1-4;
$R^2$ is an alkyl group having 1-6 carbons;
X is O, S, Se or NR$^{15}$, where $R^{15}$ is H or an alkyl group having 1-6 carbons; or X is CR$^{16}$R$^{17}$ where $R^{16}$ and $R^{17}$, which may be the same or different, are independently alkyl groups having 1-6 carbons, or $R^{16}$ and $R^{17}$ taken in combination complete a five or six membered saturated ring;
n=0, 1 or 2;
Z$^-$ is a biologically compatible counter ion;
Q has the ;formula Q1 or Q2

(Q1)

-continued

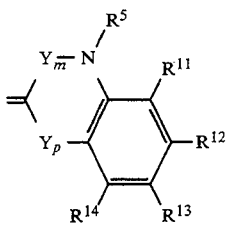
(Q2)

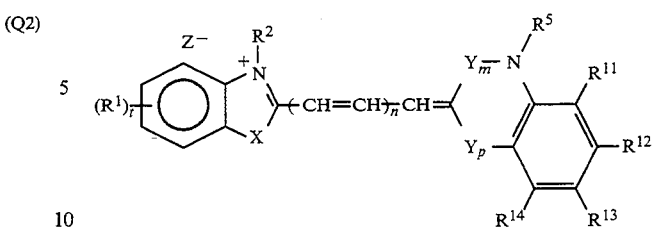

wherein

Y is —CR³=CR⁴—;

p and m=0 or 1, such that p+m=1;

$R^5$ is an alkyl, alkenyl, polyalkenyl, alkynyl or polyalkynyl group having 1-6 carbons; or $R^5$ is an OMEGA;

$R^3$, $R^4$, $R^6$ and $R^7$, which may be the same or different, are independently H; or an alkyl, alkenyl, polyalkenyl, alkynyl or polyalkynyl group having 1-6 carbons; or a halogen; or —OH, —OR⁸, —SR⁸, —(NR⁸R⁹); or —OSO₂R¹⁹ where $R^{19}$ is alkyl having 1-6 carbons, or perfluoroalkyl having 1-6 carbons or aryl; or an OMEGA;

or $R^6$ and $R^7$, taken in combination are —(CH₂)ᵥ— where v=3 or 4, or $R^6$ and $R^7$ form a fused aromatic ring according to formula Q2;

$R^{11}$, $R^{12}$, $R^{13}$, and $R^{14}$, which may be the same or different, are independently H; or an alkyl, alkenyl, polyalkenyl, alkynyl or polyalkynyl group having 1-6 carbons; or a halogen; or an OMEGA: or —OH, —OR⁸, —SR⁸, or —(NR⁸R⁹);

OMEGA is a saturated or unsaturated substituted or unsubstituted, cyclic substituent that has a total of 3-16 ring carbon atoms in 1-2 alicyclic, heteroalicyclic, aromatic, or heteroaromatic rings, containing 1-4 heteroatoms wherein the hetero atoms are O, N or S, that is unsubstituted or optionally substituted by halogen, alkyl, perfluoroalkyl, amino, alkylamino, dialkylamino, alkoxy or carboxyalkyl, having 1-16 carbons, and that is attached as $R^3$, $R^4$, $R^5$, $R^6$, $R^7$, $R^{11}$, $R^{12}$, $R^{13}$, or $R^{14}$ by a single bond; such that at least one of $R^3$, $R^4$, $R^5$, $R^6$, $R^7$, $R^{11}$, $R^{12}$, $R^{13}$, and $R^{14}$ is an OMEGA, and, where more than one of $R^3$, $R^4$, $R^5$, $R^6$, $R^7$, $R^{11}$, $R^{12}$, $R^{13}$, and $R^{14}$ is an OMEGA, each OMEGA is optionally the same or different.

b) incubating the sample for a time sufficient for the dye compound to combine with the nucleic acid in the sample to form a nucleic acid-dye complex that gives a detectable fluorescent signal;

c) observing the detectable fluorescent signal of the nucleic acid-dye complex.

50. A method according to claim 49, of staining nucleic acids in a sample, wherein the nucleic acids are enclosed in a biological structure, comprising a) combining a sample that contains nucleic acids, wherein the nucleic acids are enclosed in a biological structure, with a dye compound of the formula:

b) incubating the sample for a time sufficient for the dye compound to combine with the nucleic acid in the sample to form a nucleic acid-dye complex that gives a detectable fluorescent signal;

c) observing the detectable fluorescent signal of the nucleic acid-dye complex.

51. A method according to claim 49, of staining nucleic acids in a sample, wherein the nucleic acids are not enclosed in a biological structure, comprising a) combining a sample that contains nucleic acids, wherein the nucleic acids are not enclosed in a biological structure, with a dye compound of the formula:

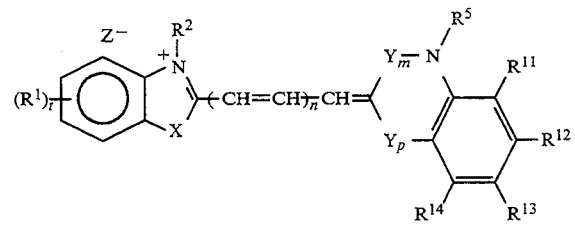

b) incubating the sample for a time sufficient for the dye compound to combine with the nucleic acid in the sample to form a nucleic acid-dye complex that gives a detectable fluorescent signal;

c) observing the detectable fluorescent signal of the nucleic acid-dye complex.

52. A method according to claim 49, wherein the sample is an electrophoretic gel.

53. A pyridinium or quinolinium salt of the formula:

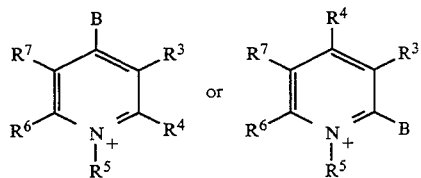

or of the formula:

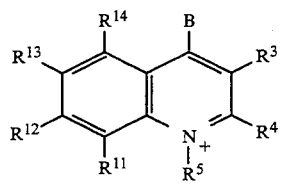

or

-continued

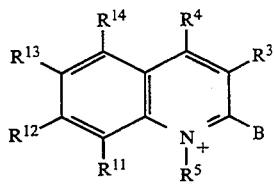

wherein $R^5$ is an OMEGA;

B is methyl;

$R^6$ and $R^7$ are H:

$R^3$, $R^{11}$, $R^{12}$, $R^{13}$, and $R^{14}$ are independently H or alkyl having 1-6 carbons $R^4$ is F, Cl, Br, I, or —$OSO_2R^{19}$ where $R^{19}$ is alkyl having 1-6 carbons, or perfluoroalkyl having 1-6 carbons, or aryl.

54. A cyclic-substituted unsymmetrical cyanine dye, comprising a first heterocyclic ring system that is a substituted benzothiazolium, benzoxazolium, benzoselenazolium, benzimidazolium, or dialkylindolinium; That is linked by a monomethine, trimethine, or pentamethine bridging moiety attached at the 2-position of said first ring system to the 2- or 4- position of a second heterocyclic ring system that is a substituted quinolinium or that is linked by a monomethine bridging moiety attached to the 2-position of a second heterocyclic ring system that is a substituted pyridinium; wherein one or more substituents of said second ring system is an OMEGA, where OMEGA is a substituted or unsubstituted cyclohexyl, cyclohexenyl, morpholino, piperidinyl, naphthyl, phenyl, thienyl, benzothizolyl, furanyl, oxazolyl, benzoxazolyl or pyridinyl.

* * * * *

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 2 line 53 | Set. SHOULD BE Ser. |
| col 2 line 65 | hmily SHOULD BE family |
| col 3 line 9 | elcctrophoretic SHOULD BE electrophoretic |
| col 3 line 44 | pans SHOULD BE parts |
| col 3 line 46 | roethine SHOULD BE methine |
| col 3 line 48 | sUbstituents SHOULD BE substituents |
| col 3 line 62 | thionyls SHOULD BE thienyls |
| col 4 line 31 | biomolccules SHOULD BE biomolecules |
| col 4 line 41 | independently having SHOULD BE independently H or alkyl groups having |
| col 4 line 48 | dclocalization SHOULD BE delocalization |
| col 4 line 51 | pentamcthine SHOULD BE pentamethine |
| col 4 line 67 | bascd SHOULD BE based |
| col 4 line 67 | hctcrocycle SHOULD BE heterocycle |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 5 line 20 | substitucnts SHOULD BE substituents |
| col 5 line 25 | $-OSO_2{}^{R19}$ SHOULD BE $-OSO_2R^{19}$ |
| col 5 line 29 | 4,:forming SHOULD BE 4, forming |
| col 5 line 49 | polyalkcnyl SHOULD BE polyalkenyl |
| col 6 line 12 | $-OSO_2R_{19}$ SHOULD BE $-OSO_2R^{19}$ |
| col 6 line 14 | $NR^8R^9$ SHOULD BE $-NR^8R^9$ |
| col 6 line 34 | ill SHOULD BE in |
| col 6 line 65 | unsuccessfifl SHOULD BE unsuccessful |
| col 7 line 28 | ofbiomolecules SHOULD BE of biomolecules |
| col 7 line 30 | nuclcic SHOULD BE nucleic |
| col 8 line 18 | individuai SHOULD BE individual |
| col 9 lines 8-9 | cytomcters SHOULD BE cytometers |
| col 9 line 11 | elcctrophoresis SHOULD BE electrophoresis |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 9 line 19 | 3 10 SHOULD BE 310 |
| col 9 line 55 | sensitivily SHOULD BE sensitivity |
| col 9 line 57 | nuclcic SHOULD BE nucleic |
| col 11 table 4 footer 2 | ($K_o$ SHOULD BE ($K_p$) |
| col 11 table 4 footer 4 | 0.05 0D SHOULD BE 0.05 OD |
| col 12 table 6 col n | I SHOULD BE 1 |
| col 13 line 62 | benzoselcnazolium SHOULD BE benzoselenazolium |
| col 13 line 63 | benzirnidazolium SHOULD BE benzimidazolium |
| col 15 line 9 | qninolinium SHOULD BE quinolinium |
| col 15 line 12 | qninolinium SHOULD BE quinolinium |
| col 15 line 23 | benzopyridincs SHOULD BE benzopyridines |
| col 15 line 24 | bcnzopyridinium SHOULD BE benzopyridinium |
| col 16 line 13 | snbscripts SHOULD BE subscripts |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 16 line 14 | merebored SHOULD BE membered |
| col 16 line 64 | quinolonc SHOULD BE quinolone |
| col 16 line 64 | convened SHOULD BE converted |
| col 17 line 5 | convened SHOULD BE converted |
| col 17 line 8 | thiols SHOULD BE thiols |
| col 17 line 34 | dchydroxylated SHOULD BE dehydroxylated |
| col 17 line 36 | 10) SHOULD BE 30) |
| col 17 line 41 | convened SHOULD BE converted |
| col 17 line 42 | flirther SHOULD BE further |
| col 17 line 46 | roethine SHOULD BE methine |
| col 17 line 46 (again) | roethine SHOULD BE methine |
| col 17 line 55 | bcnzazolium SHOULD BE benzazolium |
| col 18 line 5 | o:f SHOULD BE of |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 18 line 7 | dii sopropylethylami he. SHOULD BE diisopropylethylamine. |
| col 18 line 9 | roethine SHOULD BE methine |
| col 18 line 27 | trimethinc SHOULD BE trimethine |
| col 19 line 1 | arthydride SHOULD BE anhydride |
| col 19 line 4 | O SHOULD BE $\phi$ |
| col 19 line 25 | dikctene SHOULD BE diketene |
| col 19 line 28 | mmolcs SHOULD BE mmoles |
| col 19 line 39 | 1.,2- SHOULD BE 1,2- |
| col 20 line 10 | -4-methyl, 1- SHOULD BE -4-methyl-1- |
| col 20 line 21 | phcnylamine SHOULD BE phenylamine |
| col 20 line 21 | methylatcd SHOULD BE methylated |
| col 20 line 41 | phcnylaniline SHOULD BE phenylaniline |
| col 20 line 55   I- | *should appear directly above* SEt *and to the right of the vertical bond connecting* Et *with* N$^+$ |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 20 line 60 | Nail SHOULD BE NaH |
| col 20 line 67 | 2:15 SHOULD BE 2.15 |
| col 20 line 68 | obcnzothiazole SHOULD BE obenzothiazole |
| col 21 line 37 | [-1,2 SHOULD BE ]-1,2 |
| col 22 line 12 | glueing SHOULD BE eluting |
| col 22 line 13-14 | re-strange SHOULD BE red/orange |
| col 22 line 42 | quinolene SHOULD BE quinolone |
| col 23 line 59 | Example 1 SHOULD BE Example 7 |
| col 24 line 16 | Example 6 SHOULD BE Example 10 |
| col 24 line 31 | preparation SHOULD BE Preparation |
| col 24 line 33 | thiazole SHOULD BE thiazol |
| col 24 line 64 | chide SHOULD BE crude |
| col 24 line 67 | rccrystal- SHOULD BE recrystal- |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 25 line 3 | thiazole SHOULD BE thiazol |
| col 25 line 5 | 5 103 SHOULD BE 5103 |
| col 25 line 64 | chloroforum SHOULD BE chloroform |
| col 26 line 28 | methylobenzoxazolium SHOULD BE methyl-benzoxazolium |
| col 27 line 2 | convened SHOULD BE converted |
| col 28 line 16 | Example 3 SHOULD BE Example 10 |
| col 28 line 55 | of2- SHOULD BE of 2- |
| col 29 line 36 | m vacuo SHOULD BE in vacuo |
| col 31 line 4 | (dye 780) SHOULD BE (dye 780(Cl)) |
| col 31 line 61-62 | C., mL SHOULD BE C., 0.4 mL |
| col 33 lines 33-34 | varia-blyosized SHOULD BE variably-sized |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 33 line 44 | 10-30 rain SHOULD BE 10-30 min |
| col 33 line 59 | ciliates. SHOULD BE ciliates, |
| col 33 line 62 | spermalozoans SHOULD BE spermatozoans |
| col 34 line 1 | the.dye SHOULD BE the dye |
| col 34 line 9 | Dulbccco's SHOULD BE Dulbecco's |
| col 34 line 16 | epifiuoresccnce SHOULD BE epifluorescence |
| col 34 line 29 | homodimcr SHOULD BE homodimer |
| col 34 line 31 | cylometry SHOULD BE cytometry |
| col 34 line 38 | :for SHOULD BE for |
| col 34 line 38 | rain SHOULD BE min |
| col 34 line 39 | cytometcr SHOULD BE cytometer |
| col 34 line 45 | Rcticulocyte SHOULD BE Reticulocyte |
| col 34 line 47 | Chex. SHOULD BE Chex, |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 34 line 48 | rcticulocytes SHOULD BE reticulocytes |
| col 34 line 49 | rcticulocyte SHOULD BE reticulocyte |
| col 34 line 51 | hcmolytic SHOULD BE hemolytic |
| col 35 line 27 | solntion SHOULD BE solution |
| col 35 line 31 | epifluorcscence SHOULD BE epifluorescence |
| col 35 line 37 | resultsin SHOULD BE results in |
| col 35 line 59 | *coil* SHOULD BE *coli* |
| col 35 line 62 | bacterial SHOULD BE bacteria/mL |
| col 36 line 11 | :foregoing SHOULD BE foregoing |
| col 36 line 32 | allcyclic SHOULD BE alicyclic |
| col 36 line 33 | heterouromatic SHOULD BE heteroaromatic |
| col 36 line 33 | nngs SHOULD BE rings |
| col 36 line 41 | -$NR^{15}$ SHOULD BE $NR^{15}$ |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 37 line 2 | p+m=t SHOULD BE p+m=1 |
| col 37 line 4 | lyailkynyl SHOULD BE lyalkynyl |
| col 37 line 4 | aa SHOULD BE an |
| col 37 lines 6-7 | dillSrent SHOULD BE different |
| col 37 line 8 | polyatlcynyl SHOULD BE polyalkynyl |
| col 37 line 28 | independently H, SHOULD BE independently H; |
| col 37 line 37 | areinc SHOULD BE amino |
| col 37 line 42 | $R^{14}$,is SHOULD BE $R^{14}$ is |
| col 37 line 46 | O has SHOULD BE Q has |
| col 37 line 58 | ($NR^8R^9$) SHOULD BE -($NR^8R^9$) |
| col 37 line 62 | iS SHOULD BE is |
| col 38 line 28 | O SHOULD BE 0   (2nd occurrence). |
| col 38 line 57 | 14 SHOULD BE 1-4 |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 38 line 59 | $-(CH_2)_2-L-(CH_2)_2'$ SHOULD BE $-(CH_2)_2-L-(CH_2)_2-$ |
| col 38 line 59 | L=O- SHOULD BE L=-O- |
| col 39 line 39 | 1-6 carbons: SHOULD BE 1-6 carbons; |
| col 39 line 40 | 1-2 aft cyclic SHOULD BE 1-2 alicyclic |
| col 39 line 57 | counter ion SHOULD BE counterion |
| col 40 line 51 | DNA SHOULD BE RNA |
| col 41 line 8 | $-(NR^8R^9)$; or or an OMEGA; SHOULD BE $-(NR^8R^9)$; or $-OSO_2R^{19}$; or an OMEGA; |
| col 41 line 10 | 0or 1 SHOULD BE 0 or 1 |
| col 41 line 58 | alkyl group SHOULD BE alkyl groups |
| col 41 line 67 | or aryl; SHOULD BE or aryl; or an OMEGA; |
| col 42 line 40 | alkyl groups SHOULD BE or alkyl groups |
| col 42 line 45 | $-NR_{10}'$, SHOULD BE $-NR_{10}-$, |
| col 42 line 56 | or2 SHOULD BE or 2 |

UNITED STATES PATENT AND TRADEMARK OFFICE
CERTIFICATE OF CORRECTION

PATENT NO. : 5,436,134
DATED : July 25, 1995
INVENTOR(S) : Haugland, et al.

It is certified that error appears in the above-indentified patent and that said Letters Patent is hereby corrected as shown below:

| | |
|---|---|
| col 42 line 58 | counter ion SHOULD BE counterion |
| col 42 line 59 | the ;formula SHOULD BE the formula |
| col 43 line 46 | 1-16 SHOULD BE 1-6 |
| col 45 line 16 | are H: SHOULD BE are H; |
| col 45 line 20 | 1-6 carbons SHOULD BE 1-6 carbons; and |
| col 46 line 8 | That is SHOULD BE that is |
| col 46 line 18 | benzothizolyl SHOULD BE benzothiazolyl |

Signed and Sealed this

Twenty-second Day of October, 1996

Attest:

BRUCE LEHMAN

*Attesting Officer*     *Commissioner of Patents and Trademarks*